United States Patent
Mynar et al.

(10) Patent No.: US 9,249,275 B2
(45) Date of Patent: Feb. 2, 2016

(54) POLYIONIC DENDRIMER AND HYDROGEL COMPRISING SAME

(71) Applicant: JAPAN SCIENCE AND TECHNOLOGY AGENCY, Kawaguchi-shi, Saitama (JP)

(72) Inventors: Justin Mynar, Thuwal (SA); Takuzo Aida, Tokyo (JP)

(73) Assignee: JAPAN SCIENCE AND TECHNOLOGY AGENCY, Saitama (JP)

(*) Notice: Subject to any disclaimer, the term of this patent is extended or adjusted under 35 U.S.C. 154(b) by 0 days.

(21) Appl. No.: 14/252,151

(22) Filed: Apr. 14, 2014

(65) Prior Publication Data
US 2014/0221292 A1    Aug. 7, 2014

Related U.S. Application Data

(62) Division of application No. 13/379,538, filed as application No. PCT/JP2010/004267 on Jun. 28, 2010, now abandoned.

(30) Foreign Application Priority Data

Jul. 1, 2009   (JP) .................................. 2009-156670

(51) Int. Cl.
| | | |
|---|---|---|
| *C08G 65/333* | (2006.01) | |
| *A61K 38/00* | (2006.01) | |
| *A61K 47/32* | (2006.01) | |
| *A61K 47/34* | (2006.01) | |
| *C08K 3/34* | (2006.01) | |
| *C08L 33/02* | (2006.01) | |
| *C08L 71/02* | (2006.01) | |
| *C08G 65/331* | (2006.01) | |
| *C08G 65/332* | (2006.01) | |
| *A61K 38/38* | (2006.01) | |
| *A61K 38/42* | (2006.01) | |
| *C08L 67/00* | (2006.01) | |

(52) U.S. Cl.
CPC ............ *C08K 3/346* (2013.01); *A61K 38/38* (2013.01); *A61K 38/42* (2013.01); *A61K 47/34* (2013.01); *C08G 65/331* (2013.01); *C08G 65/3322* (2013.01); *C08G 65/33396* (2013.01); *C08L 33/02* (2013.01); *C08L 71/02* (2013.01); *C08L 67/00* (2013.01)

(58) Field of Classification Search
None
See application file for complete search history.

(56) References Cited

U.S. PATENT DOCUMENTS

| | | | |
|---|---|---|---|
| 4,694,064 | A | 9/1987 | Tomalia et al. |
| 7,101,937 | B1 | 9/2006 | Frechet et al. |
| 2007/0244283 | A1 | 10/2007 | Riegel et al. |
| 2008/0039421 | A1 | 2/2008 | Chung et al. |

FOREIGN PATENT DOCUMENTS

| | | |
|---|---|---|
| JP | 63-099233 A | 4/1988 |
| JP | 7-505915 A | 6/1995 |
| JP | 7-216101 A | 8/1995 |
| JP | 2002-053629 A | 2/2002 |
| JP | 2005-213400 A | 8/2005 |
| JP | 2005-322635 A | 11/2005 |
| JP | 2002-524524 A | 11/2006 |
| JP | 2007-308500 A | 11/2007 |
| JP | 2007-530752 A | 11/2007 |
| JP | 2008-063316 A | 3/2008 |
| JP | 2008-100941 A | 5/2008 |
| JP | 2008-537499 A | 9/2008 |
| JP | 2009-046553 A | 3/2009 |
| JP | 2009-120626 A | 6/2009 |
| WO | 2004/047869 A1 | 6/2004 |
| WO | 2006/082768 A1 | 8/2006 |

OTHER PUBLICATIONS

Liu et al., "High clay content nanocomposite hydrogels with surprising mechanical strength and interesting deswelling kinetics," Polym. Commun. 47:1-5 (2006).*
Liao, "Dendrimer Graft Hyperbranched Hydrogels," J. Med. Biol. Eng'g 23:85-88 (2003).*
Wang, Q. et al., "High-water-content moldable hydrogels by mixing clay and dendritic molecular binder", Nature, Jan. 2010, pp. 339-343, vol. 463.
Ihre et al., "Fast and convenient divergent synthesis of aliphatic ester dendrimers by anhydride coupling", J. Am. Chem. Soc., 2001, vol. 123, pp. 2908-5917.
Aggeli, A. et al., "Responsive gels formed by the spontaneous self-assembly of peptides into polymeric b-sheet tapes", Nature, Mar. 1997, pp. 259-262, vol. 386.
Greenwald, Richard. et al., "Poly(ethylene glycol) Conjugated Drugs and Prodrugs: A Comprehensive Review", Crit. Rev. Ther. Drug Carrier System, 2000, pp. 101-163, vol. 17.

(Continued)

*Primary Examiner* — Julie Ha
*Assistant Examiner* — Kristina M Hellman
(74) *Attorney, Agent, or Firm* — Westerman, Hattori, Daniels & Adrian, LLP

(57) ABSTRACT

Provided is a hydrogel which includes water as the main component at a high water content and has mechanical strength suitable for practical use and which exhibits high transparency and self-healing and shape-retaining properties. Also provided are both a material for the hydrogel and a novel polyionic dendrimer. A polyionic dendrimer which includes a hydrophilic linear polymer as the core and polyester dendrons attached to both terminals of the linear polymer and in which cationic groups are bonded to the surfaces of the dendrons, the cationic groups being selected from the group consisting of guanidine group, thiourea group, and isothiourea group; a material for a hydrogel, which includes the polyionic dendrimer and clay; and a hydrogel prepared using the material.

16 Claims, 6 Drawing Sheets
(5 of 6 Drawing Sheet(s) Filed in Color)

(56) References Cited

OTHER PUBLICATIONS

Haraguchi, Kazutoshi et al., "Control of the Coil-to-Globule Transition and Ultrahigh Mechanical Properties of PNIPA in Nanocomposite Hydrogels", Angewandte Chemie, 2005, pp. 6500-6504, vol. 44.

Hirst, Andrew, "High-Tech Applications of Self-Assembling Supramolecular Nanostructured Gel-Phase Materials: From Regenerative Medicine to Electronic Devices", Angewandte Chemie, 2008, pp. 8002-8018, vol. 47.

Nowak, Andrew et al., "Rapidly recovering hydrogel scaffolds from self-assembling diblock copolypeptide amphiphiles", Nature, May 2002, pp. 424-428, vol. 417.

Rockwood Additives Ltd., Laponite in Personal Care Products , Laponite Technical Bulletin L211/01g, 1990.

Yoshida, Masaru et al., "Oligomeric Electrolyte as a Multifunctional Gelator", JACS Commuincations, 2007, pp. 11039-11041, vol. 123.

Zhang, S. "Fabrication of Novel Biomaterials Through Molecular Self-Assembly", Nature Biotechnology, Oct. 2001, pp. 1171-1178, vol. 21.

International Search Report of PCT/JP2010/004267, mailing date Sep. 28, 2010.

Notification of Transmittal of Translation of the International Preliminary Report on Patentability (Forms PCT/IB/338) of International Application No. PCT/JP2010/004267 mailed Feb. 23, 2012 with forms PCT/IB/373, PCT/ISA/237 and PCT/IB/326.

Extended European Search Report dated Oct. 19, 2012, issued in corresponding Euroepan Patent Application No. 10793831.8 (11 pages).

Chung et al., "Dendritic Oligoguanidines as Intracellular Translocators", Biopolymers, New York, NY, US, vol. 76, No. 1, Jan. 1, 2004; pp. 83-96, XP002547028.

Tsogas et al., "Interaction and Transport of Poly(-lysine) Dendrigrafts throgh Liposomal and Cellular Membranes: The Role of Generation and Surface Functionalization"; Biomacromolecules, vol. 8, No. 10; Oct. 1, 2007, pp. 3263-3270, XP55040617.

Okuro et al., "Molecular glues carrying multiple guanidinium ion pendants via an oligoether spacer: stabilization of microtubules against depolymerization", J. Am. Chem. Soc., 2009, vol. 131, pp. 1626-1627.

Namazi et al., "Dendrimers of citric acid and poly(ethylene glycol) as the new drug delivery systems", Biomaterials, 2005, vol. 26, pp. 1175-1183.

Chen et al., "Cytotoxicity, hemolysis, and acute in vivo toxicity of dendrimers based on melamine, candidate vehicles for drug delivery," J. Am. Chem. Soc., 2004, vol. 126, pp. 10044-10048.

Wender et al., "Dendrimeric molecular transporters: synthesis and evaluatiation of tunable polyguanididno dendrimers that faciliate cellular uptake", Org. Lett, 2005, vol. 7, pp. 4815-4818.

\* cited by examiner

POLYIONIC DENDRIMER AND HYDROGEL COMPRISING SAME

CROSS-REFERENCE TO RELATED APPLICATION

This application is a Divisional of copending application Ser. No. 13/379,538, filed Dec. 20, 2011, which is a 371 of PCT International Application No. PCT/JP2010/004267 filed on Jun. 28, 2010, which based upon and claims the benefit of priority of the prior Japanese Patent Application No. 2009-156670, filed on Jul. 1, 2009. The entire contents of each of the above documents are hereby incorporated by reference into the present application.

TECHNICAL FIELD

The present invention relates to a novel polyionic dendrimer. The invention also relates to a material for hydrogel that contains the polyionic dendrimer and clay minerals (i.e., clay) and a hydrogel obtained by including a great amount of water in the material for hydrogel.

BACKGROUND ART

Water is an essential component for living organisms on earth and it is regarded as a symbol of pureness and cleanness. 71% of the surface of earth is covered with water and 65% of a human body is composed of this simple yet fully active molecule. In nature, especially in a biological world, water plays an important role. As such, if a water-retaining material with high water retention rate is produced, it can be used as an important material having a positive effect on environment and broad spectrum of use. Until now, an attempt to produce a water-retaining material with high water retention rate was not so successful due to poor mechanical strength as easily expected. However, focusing on a potential possibility of using a material containing water as a main component, for drug delivery or an artificial cartilage, and the like, several research groups succeeded in improving the mechanical strength of a material (Non-patent Documents 1 to 3).

The polymer hydrogel conventionally known as a water-retaining material is basically produced by crosslinking based on covalent bond. The polymer hydrogel that is crosslinked by a conventional method of organic chemistry is an opaque and soft material with low strength and also it has no self-restoring property.

To improve the strength of a hydrogel, an organic and inorganic hybrid hydrogel which has improved tensile fracture strength by a method of polymerizing (meth)acrylamide derivatives in the presence of clay minerals is suggested (Patent Document 1). Furthermore, it is also reported that the strength is improved by having a copolymer with a polymerizable monomer having a carboxylic acid group or a sulfonic acid group (Patent Document 2).

Furthermore, a polymer/inorganic hybrid nano composite hydrogel wherein a polymer is composited with water-swellable clay minerals is now drawing attention as it exhibits relatively good mechanical strength. However, the water retention rate of these gels is only 90% and the mechanical strength decreases as the water retention rate increases. Thus, to obtain practically meaningful strength, it is necessary to decrease the water retention rate to 80% or so (Non-patent Document 4).

As polymerization or crosslinking is required to produce conventionally known polymer hydrogels, it is necessary to perform a complicated process such as repeated heating or cooling cycle. For example, it is reported that a hydrogel can be obtained by dehydration and reswelling of an agglomerate which is obtained by maintaining polyvinyl alcohol with saponification degree of 90% or higher under a pressure of 1.2 to 5.0 atm at 105 to 150° C. in the presence of steam (Patent Document 3).

Such hydrogel is used in many areas of industry including pharmaceuticals, food products, cosmetics, hygienic products, agricultural materials, electronic materials, and the like. For example, there is a pharmaceutical agent obtained by containing GM-CSF in a hydrogel made of polylactic acid and the like (Patent Document 4), a joint supplemental preserving material containing a photo-crosslinkable and biodegradable hydrogel using oligo (poly(ethylene glycol)fumarate) (Patent Document 5), a biomaterial having a morphology developing property on an account of a polymer-crystal based hydrogel of a polymer having a linear polyethyleneimine skeleton (Patent Document 6), a polymer hydrogel electrolyte for an alkaline battery made of polyvinyl alcohol, an anionic crosslinked polymer, and alkali hydroxide (Patent Document 7), and a hydrogel comprising an ionic organic compound having a quaternary ammonium cation which is formed from a heterocyclic compound such as pyridine (Patent Document 8), and the like.

For an application to pharmaceuticals and food products, and the like, human safety is required. Further, from the viewpoint of environment protection, biodegradability is required. As such, it is desired for the hydrogel-constituting materials to satisfy such requirements. For example, it is known that polyethylene glycol or a certain kind of polyester is readily discharged from a human body or it is biologically easily degradable (Non-patent Documents 5 and 6). It is also known that a clay nano sheet, which has as a source material inorganic minerals that are present in nature, is a safe material widely used in cosmetics such as lotion, tooth paste, shampoo, shower gel, and the like (Non-patent Document 7). In this connection, development of a hydrogel using these materials is waited for.

Meanwhile, "dendrimer" indicates a tree-shaped polymer having a regularly branched structure stemming from a core, and the name comes from the Greek word meaning a tree. A dendrimer is composed of a center molecule called core and a side chain called dendron. The number of the repeating branching cycles in a dendron part is described as generation. In general, a polymer has a certain molecular weight distribution, and a dendrimer of higher generation has a unique characteristic that it has almost single molecular weight even though the molecular weight is close to several tens of thousands. As the core is covered with dendron and in an environment isolated from the outside, it is found to exhibit a unique light-emitting behavior or reactivity, and therefore its use as a new functional material is expected. However, as the synthesis is very difficult compared to other polymers, it is not practically usable yet. The PAMAM dendrimer, and the like, which has a polyamidoamine structure and is now used widely, is commercially obtainable from a drug company (source: free encyclopedia "Wikipedia").

Until now, no application of a dendrimer on hydrogel is made. However, application on DDS and the like is expected. Furthermore, it is reported that an ionic dendrimer in which a cation or an anion such as ammonium ion and carboxylate ion is bonded to the surface of a dendrimer such as PAMAM dendrimer is useful as an anti-parasitic composition (Patent Document 9).

PRIOR ART DOCUMENTS

Patent Documents

Patent Document 1: Japanese Patent Application Laid-Open (JP-A) No. 2002-53629
Patent Document 2: JP-A No. 2009-46553
Patent Document 3: JP-A No. 7-216101
Patent Document 4: JP-A No. 2007-308500
Patent Document 5: Japanese Patent Application National Publication (Laid-Open) No. 2008-537499
Patent Document 6: JP-A No. 2005-213400
Patent Document 7: JP-A No. 2005-322635
Patent Document 8: International Publication No. WO2006/082768
Patent Document 9: Japanese Patent Application National Publication (Laid-Open) No. 2002-524524

Non-Patent Documents

Non-patent Document 1: Zhang, S., Nat. Biotechnol. 21, p. 1171-1178 (2003)
Non-patent Document 2: Aggell, A. et al., Nature 386, p. 259-262 (1997)
Non-patent Document 3: Hirst, A. R. et al., Angew. Chem. Int. Ed. 47, p. 8002-8018 (2008)
Non-patent Document 4: Haraguchi, K. et al., Angew. Chem. Int. Ed. 44, p. 6500-6504 (2005)
Non-patent Document 5: Greenwald, R. B. et al., Crit. Rev. Ther. Drug Carrier Syst. 17, p. 101-163 (2000)
Non-patent Document 6: Ihre, H. et al., J. Am. Chem. Soc. 123, p. 5908 (2001)
Non-patent Document 7: Rockwood Additives Ltd., Laponite in personal care products Laponite technical bulletin L211/01 g (1990)
Non-patent Document 8: H. Ihre, et al., J. Am. Chem. Soc. 123, p. 5908 (2001)
Non-patent Document 9: Yoshida, M. et al., J. Am. Chem. Soc. 129, p. 11039-11041 (2007)
Non-patent Document 10: Nowak, A. P. et al., Nature 417, p. 424-428 (2002)

SUMMARY OF THE INVENTION

Problems to be Solved by the Invention

The invention provides a hydrogel which overcomes the problems of conventional hydrogels described above, contains water as a main component, and has a high water content and mechanical strength suitable for practical use, and also provides a material for the hydrogel. Further, the invention provides a hydrogel which exhibits high transparency and self-restoring and shape-retaining properties, and a material for the hydrogel. Still further, the invention provides a novel polyionic dendrimer.

Means for Solving the Problems

The inventors of the invention extensively studied to develop a material which overcomes the problems of conventional hydrogels and contains water as a main component to have mechanical strength suitable for practical use. As a result, the inventors established a method of molecular designing and synthesizing a polyionic dendrimer which has a hydrophilic linear polymer such as polyethylene glycol in the core part and polyester dendrons attached to both terminals of the linear polymer so that cationic groups such as guanidine group are present on the surfaces of the dendrons. It was also found by the inventors that a hydrogel of a composite, which is obtained by binding of the polyionic dendrimer to the surface of clay minerals (i.e., clay) having a nano sheet structure via electrostatic interaction and a hydrogen bond and the like, has high mechanical strength and an instantaneous and complete self-restoring property, and combined use of a linear polymer having an ionic side chain can yield higher mechanical strength. Accordingly, the inventors accomplished the present invention.

Specifically, the invention relates to a polyionic dendrimer which has a hydrophilic linear polymer such as polyethylene glycol as the core and polyester dendrons attached to both terminals of the linear polymer and in which cationic groups are bonded to the surfaces of the dendrons, the cationic groups being selected from a guanidine group, a thiourea group, and/or an isothiourea group.

Further, the invention relates to a material for hydrogel containing the polyionic dendrimer of the invention described above and clay minerals (i.e., clay), and a hydrogel containing water.

Further, the invention relates to a material for hydrogel containing the polyionic dendrimer of the invention described above, clay minerals (i.e., clay), and a linear polymer having an ionic side chain, and to a hydrogel containing water.

Still further, the invention relates to a protein-containing hydrogel containing a physiologically active protein in any one of the hydrogels of the invention described above.

The detailed explanations of the invention are given below.

(1) A polyionic dendrimer, comprising: a hydrophilic linear polymer as the core, and dendrons attached to both terminals of the linear polymer, wherein a cationic group selected from the group consisting of a guanidine group, a thiourea group, and an isothiourea group is bonded to a surface of the dendron.

(2) A polyionic dendrimer, comprising: a hydrophilic linear polymer as the core, and dendrons attached to both terminals of the linear polymer, wherein a cationic group selected from the group consisting of a guanidine group, a thiourea group, and an isothiourea group is bonded to a surface of the dendron.

(3) The polyionic dendrimer according to (2) described above, wherein the polyester is a polyester composed of a saturated aliphatic carboxylic acid having 3 to 10 carbon atoms in which two or more hydroxyl groups are symmetrically substituted to have symmetric branching.

(4) The polyionic dendrimer according to any one of (1) to (3) described above, wherein the hydrophilic linear polymer as the core is a polyalkylene glycol.

(5) The polyionic dendrimer according to any one of (1) to (4) described above, wherein a cationic group selected from the group consisting of a guanidine group, a thiourea group, and an isothiourea group is bonded to the surface of the dendron via a polyether group.

(6) The polyionic dendrimer according to any one of (1) to (4) described above, wherein the polyionic dendrimer is a polyionic dendrimer that is represented by the following formula 1:

[Chemical Formula 1]

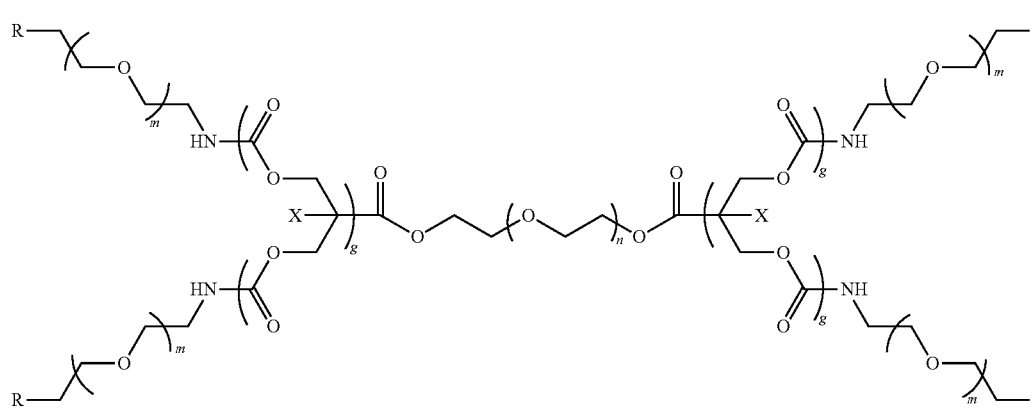

Formula 1

(in the formula, n represents the repeating number of polyethylene glycol in the core and is from 20 to 100000, m represents the repeating number of a linker group for introducing cationic groups to the surface and is from 1 to 6, g represents the generation of the dendron and is from 1 to 5, R represents a cationic group selected from the group consisting of a guanidine group, a thiourea group, and an isothiourea group, and X represents a hydrogen atom or a $C_1$-$C_7$ alkyl group).

(7) The polyionic dendrimer according to (6) described above, wherein the polyhydroxy carboxylic acid including X in the formula 1 is a saturated aliphatic carboxylic acid having 3 to 10 carbon atoms in which two or more hydroxyl groups are symmetrically substituted to have symmetric branching.

(8) The polyionic dendrimer according to (6) or (7) described above, wherein X in the formula 1 is a methyl group.

(9) The polyionic dendrimer according to any one of (1) to (8) described above, wherein the cationic group selected from the group consisting of a guanidine group, a thiourea group, and an isothiourea group is a cationic group represented by the following formula 2, formula 3, or formula 4:

[Chemical Formula 2]

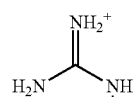

Formula 2

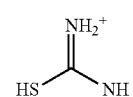

Formula 3

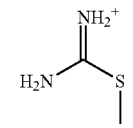

Formula 4

(10) The polyionic dendrimer according to any one of (1) to (9) described above, wherein the polyionic dendrimer is a polyionic dendrimer that is represented by the following formula 5:

[Chemical Formula 3]
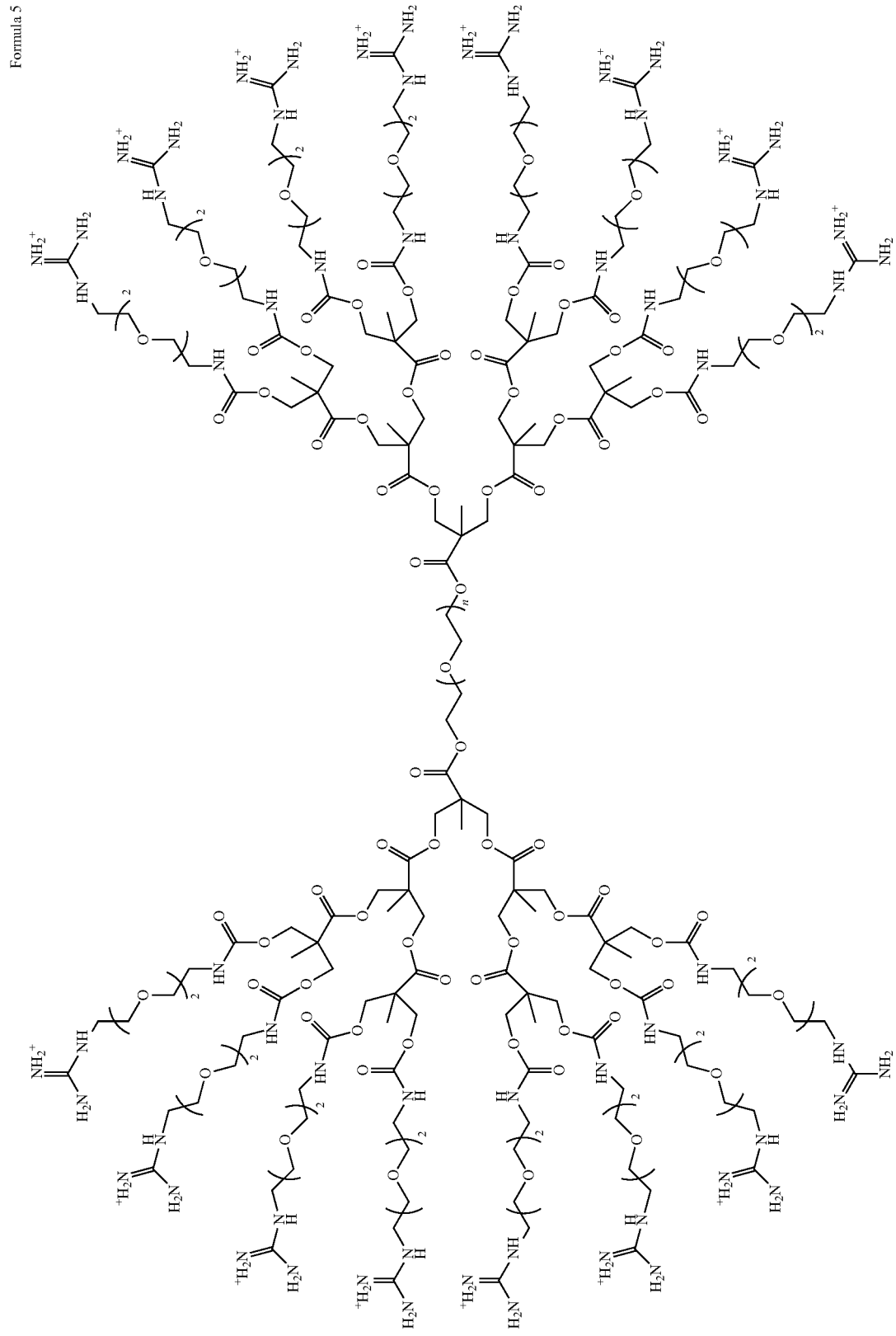
Formula 5

(in the formula, n is from 20 to 100000).

(11) A material for a hydrogel, comprising: the polyionic dendrimer according to any one of (1) to (10) described above and a clay mineral.

(12) The material for a hydrogel according to (11) described above, further comprising a linear polymer having an ionic side chain.

(13) The material for a hydrogel according to (12) described above, wherein linear polymer having an ionic side chain is an alkali metal salt of polyacrylic acid or polymethacrylic acid.

(14) The material for a hydrogel according to any one of (11) to (13) described above, wherein the clay mineral is a clay mineral selected from the group consisting of a water-swellable smectite and a layer silicate salt.

(15) The material for a hydrogel according to any one of (11) to (14) described above, wherein the clay mineral is a clay mineral having a nano sheet structure.

(16) The material for a hydrogel according to any one of (11) to (15) described above, wherein the clay mineral is one or more kinds selected from the group consisting of montmorillonite, hectorite, saponite, bidelite, mica, and synthetic mica.

(17) The material for a hydrogel according to (16) described above, wherein the clay mineral is a hectorite.

(18) A hydrogel, comprising: water in the material for a hydrogel according to any one of (11) to (17) described above.

(19) The hydrogel according to (18) described above, wherein a water content is 80% or more relative to the material for a hydrogel.

(20) A protein-containing hydrogel, comprising: a physiologically active protein in the hydrogel according to (18) or (19) described above.

(21) The protein-containing hydrogel according to (20) described above, wherein the physiologically active protein is myoglobin or albumin.

Effects of the Invention

The invention is to provide a polyionic dendrimer in which cationic groups are bonded to the surface, and a hydrogel using the dendrimer.

According to the invention, a tough and transparent hydrogel which can contain at least 94% of moisture and is gellified only with noncovalent bond can be provided. Further, as such water-retaining material with high water content can be introduced with a protein without compromising its biological activity and there is no decrease in mechanical strength caused by introduction of a protein, the hydrogel of the invention is useful as a protein-containing hydrogel.

Further, as the hydrogel of the invention maintains a shape-retaining property even when it is immersed in an organic solvent like tetrahydrofuran, it has a characteristic of regaining the original shape even when it is dried and treated with water for re-gellation.

The supramoleucalr hydrogel obtained from the invention contains a dendrimer with a specific size. Thus, by modifying the polymerization degree of the linear polymer in the dendrimer core, generation of the dendron, and types of an ion present on the surface of dendron, molecular designing of a polyionic dendrimer with various size and shape can be made and it can be used as a component for the hydrogel. Thus, it allows designing of a broad range of physical properties. Further, the polyionic dendrimer of the invention can be easily synthesized. Further, as the hydrogel of the invention can be easily formed by simple mixing and stirring of a clay nano sheet and a polyionic dendrimer, and if necessary, a linear polymer having an ionic side chain like sodium polyacrylate (see, FIG. 1), heating or cooling cycle which is required for production of conventional polymer hydrogels is not necessary. Thus, it has a huge potential as a multi-purpose material that can be easily produced and is favorable from an environment point of view.

Specifically, the hydrogel of the invention has excellent characteristics that it has high water content (at least 94%), sufficient mechanical strength, excellent transparency, excellent shape-retaining property, anti-chemical property, and self-restoring property which guarantees regaining of the original shape after re-gellation, and it can maintain a physiologically active or enzymatically active protein and the like without altering the properties of the protein.

Further, as it is known that polyalkylene glycol, preferably polyethylene glycol, as a hydrophilic linear polymer which constitutes the core of the polyionic dendrimer constituting the hydrogel of the invention, and polyester which constitutes the dendron can be easily discharged from a human body or they are biologically easily degradable (Non-patent Documents 5 and 6), it is favorable from an environment point of view and also highly safe to human body. The clay nano sheet used for the hydrogel of the invention has, as a raw material, an inorganic minerals present in nature, and thus it is a safe material that is already widely used for cosmetics such as lotion, toothpaste, shampoo, a shower gel, and the like (Non-patent Document 7). Based on such facts, it can be said that the hydrogel of the invention is not only favorable from an environment point of view but also highly safe to human body.

BRIEF DESCRIPTION OF THE DRAWINGS

The patent or application file contains at least one drawing executed in color. Copies of this patent or patent application publication with color drawings will be provided by the Office upon request and payment of the necessary fee.

MODES FOR CARRYING OUT THE INVENTION

Figure 1:
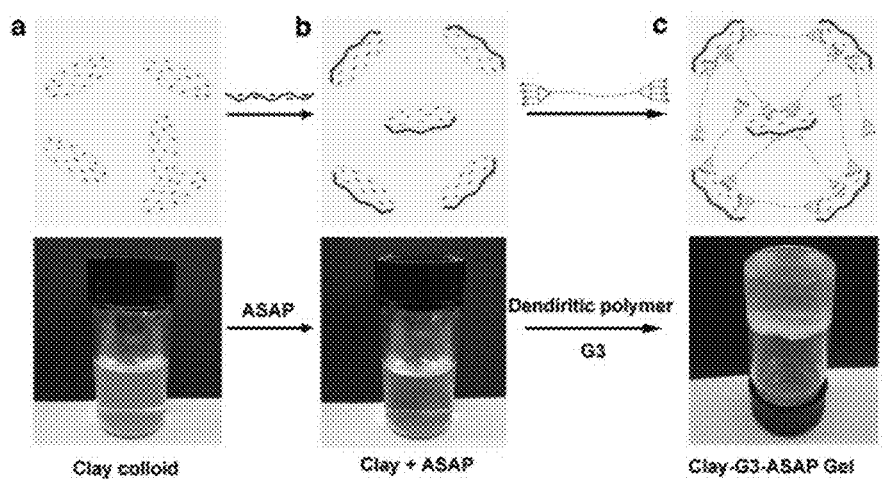
FIG. 1 includes photographic images and schematic diagrams which illustrate the production process of the hydrogel based on self-agglomeration.

The polyionic dendrimer of the invention is characterized in that it contains a hydrophilic linear polymer as the core and cationic groups are bonded to the surfaces of the dendrons attached to both terminals of the linear polymer, wherein the cationic groups are selected from the group consisting of a guanidine group, a thiourea group, and an isothiourea group.

Preferred examples of the hydrophilic linear polymer as the core include a polyalkylene glycol consisting of linear or branched alkylene glycol having 2 to 5 carbon atoms. More preferred examples of the polyalkylene glycol include polyethylene glycol. The polyalkylene glycol needs to be hydrophilic. The repeating number (n) of the alkylene glycol is, although not specifically limited, 20 to 100000, preferably 100 to 10000, more preferably 150 to 1000, and still more preferably 200 to 500. In general, when the repeating number (n) is too small, the hydrogel may have insufficient strength. On the other hand, if it is too big, the water retention rate may be impaired, and therefore it is suitably determined considering both the strength and water retention rate.

In the polyionic dendrimer of the invention, both terminals of the linear polymer in the core are dendronized. Dendronization can be achieved via any of a bond such as an ether bond (—O—), an imino bond (—N—), an ester bond (—COO—), an amide bond (—CONH—), and a carbamoyloxy bond (—OCONH—). For example, it can be achieved by using polyether based on polyol, polyamine based on polyamine, polyester based on hydroxycarboxylic acid, polyamide based on aminocarboxylic acid, or polycarbonate based on polycarbamic acid derivatives. Those with hydrophilic property and simple production method are preferable. Preferred examples of the dendronization include dendronization using polyester. Examples of the carboxylic acid used for branching in dendronization using polyester include a polyhydroxy carboxylic acid such as a dihydroxy carboxylic acid and a trihydroxy carboxylic acid. Further, to obtain symmetric branching, a carboxylic acid in which two or more hydroxyl groups are symmetrically substituted is preferable. Examples of such carboxylic acids include saturated aliphatic carboxylic acids having 3 to 10 carbon atoms, or preferably 5 to 10 carbon atoms (provided that, the carbon number excludes the carbon atoms of the carboxylic group), but not limited thereto. Preferred examples of the carboxylic acid include 3-hydroxy-2-hydroxymethyl-propionic acid and 3-hydroxy-2-hydroxymethyl-2-alkyl-propionic acid. The alkyl group is expressed as group X in the formula 1 above, and the group X represents a hydrogen atom or a $C_1$-$C_7$ alkyl group, preferably a $C_1$-$C_4$ alkyl group, and more preferably a $C_1$-$C_2$ alkyl group. Examples of the alkyl group include a linear or branched $C_1$-$C_7$, preferably $C_1$-$C_4$, and more preferably $C_1$-$C_2$ alkyl group such as a methyl group and an ethyl group. Particularly preferred examples of the carboxylic acid include a 3-hydroxy-2-hydroxymethyl-2-methyl-propionic acid.

The number of branching cycles in a dendron part is referred to as generation. The generation (g) of the polyionic dendrimer of the invention is not particularly limited. However, as the generation increases, the production becomes complicated. On the other hand, when the generation is small, the strength of the hydrogel is impaired. Thus, the generation (g) can be from 1 to 5, preferably from 1 to 4, more preferably from 2 to 3, and still more preferably 3.

By esterifying the dendrimer grown with a polyhydroxy carboxylic acid, the hydroxy group of the polyhydroxy carboxylic acid is allowed to be present on the surface of the dendrimer. In addition, according to the binding of a cationic group selected from a group consisting of a guanidine group, a thiourea group, and an isothiourea group to the hydroxy group, the polyionic dendrimer of the invention is obtained. As for a method of attaching the cationic group to the hydroxy group, a method of using an appropriate linker group is preferable. The number of the atoms in the linear chain of a linker group can be 3 to 40, preferably 6 to 30, or 6 to 20. Examples of the atom constituting the linker group include a carbon atom, an oxygen atom, and a nitrogen atom. It is sufficient for a linker group to have an ability of attaching the hydroxy group on the surface of the dendrimer to a cationic group. However, in order to maintain the hydrophilicity of the whole dendrimer, it is preferable that the linker group is also hydrophilic. Preferred examples of the linker group include polyether. The repeating number (m) of polyether is from 1 to 6, preferably from 2 to 5, more preferably from 2 to 4, and still more preferably from 2 to 3.

The bond between the linker group and the hydroxy group on the surface of the dendrimer is not specifically limited. Any of a bond such as an ether bond (—O—), an imino bond (—N—), an ester bond (—COO—), an amide bond (—CONH—), and a carbamoyloxy bond (—OCONH—) can be selected. From the viewpoint of easy producibility, the carbamoyloxy bond (—OCONH—) is preferable.

Preferred examples of the cationic group include the guanidine group, the thiourea group, and the isothiourea group that are expressed with the formula 2, the formula 3, or the formula 4 described above. More preferred examples of the cationic group include the guanidine group that is expressed with the formula 2 above.

Preferred dendronization of both terminals of the linear polymer in the polyionic dendrimer of the invention is based on the use of polyester. More preferably, it is the dendronization based on the use of the polyester that is esterified with a saturated aliphatic carboxylic acid having 3 to 10 carbon atoms, or preferably 3 to 7 carbon atoms in which two or more hydroxy groups are symmetrically substituted to give symmetric branching.

Preferred examples of the hydrophilic linear polymer in the core of the polyionic dendrimer of the invention include polyalkylene glycol. More preferred examples thereof include polyalkylene glycol having the repeating number of 20 to 100000. Still more preferred examples thereof include polyethylene glycol having the repeating number of 20 to 100000.

With respect to the preferred surface of dendron of the polyionic dendrimer of the invention, a cationic group selected from a group consisting of a guanidine group, a thiourea group, and an isothiourea group is bonded thereto via a polyether group. Preferred examples of the polyether group include polyalkylene ether with the repeating number of from 1 to 6, preferably from 2 to 5, more preferably from 2 to 4, and still more preferably from 2 to 3. More preferred examples thereof include polyethylene ether.

Preferred examples of the polyionic dendrimer of the invention include a polyionic dendrimer wherein the hydrophilic linear polymer as the core is polyalkylene glycol with repeating number of 20 to 100000, dendronization of both terminals of the linear polymer is based on the use of polyester with saturated aliphatic carboxylic acids having 3 to 10 carbon atoms in which two or more hydroxy groups are symmetrically substituted to give symmetric branching, and cationic groups are bonded to the surfaces of the dendrons via polyether group, the cationic group being selected from the group consisting of a guanidine group, a thiourea group, and an isothiourea group.

More preferred examples of the polyionic dendrimer of the invention include a polyionic dendrimer represented by the following formula 6 in which X in the formula 1 is a methyl group

[Chemical Formula 4]

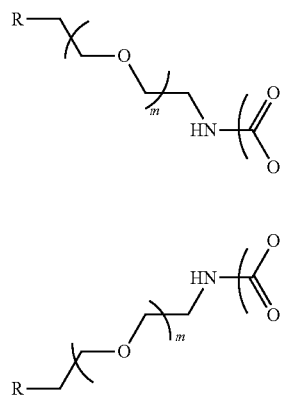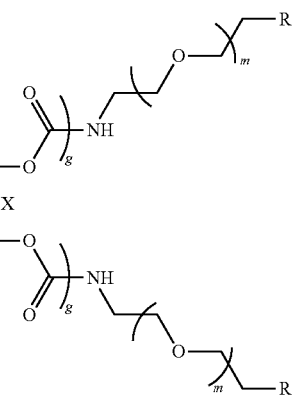

Formula 6

(in the formula, n representing the repeating number of polyethylene glycol in the core is from 20 to 100000, m representing the repeating number of a linker group for introducing a cationic group to the surface is from 1 to 6, g representing the generation of the dendron is from 1 to 5, and R represents a cationic group that is selected from the group consisting of a guanidine group, a thiourea group, and an isothiourea group).

More preferred examples of the polyionic dendrimer of the invention include the polyionic dendrimer that is represented by the formula 5 above. The generation of the polyionic dendrimer that is represented by the formula 5 is the third generation, and herein below, it is abbreviated as "G3". Similarly, the second generation polyionic dendrimer is abbreviated as "G2", and the first generation polyionic dendrimer is abbreviated as "G1". Although the repeating number of the polyether in the example of G3 represented by the formula 5 is 2, it is not limited thereto.

The polyionic dendrimer of the invention can be produced according to a method known per se in the art.

For example, a bisdendrimer which has a hydroxy group as the surface, a polyester group as the branched chain, and a highly hydrophilic polyethylene glycol group as the core is produced according to the production route shown in Example 1. The dendrimer which has a hydroxy group as the surface (abbreviated as G1-OH, G2-OH, or G3-OH) may be produced according to a known method, for example, the method described in the Document (H. Ihre, O. L. Padilla De Jesus, J. M. J. Frechet, J. Am. Chem. Soc. 123, 5908 (2001)).

By attaching an appropriate linker group to the dendrimer having a hydroxy group as the surface as produced above (i.e., G1-OH, G2-OH, or G3-OH) and derivatizing it with a cationic group such as a guanidine group, the polyionic dendrimer of the invention can be produced. As a specific example, see the method described in Examples 2 to 4 below.

A bisdendrimer having the fourth and higher generation dendron can be also produced by repeating the method of Examples 1 to 4. Further, a bisdendrimer which has a thiourenium group or an isothiourenium group on the surface can be also produced by converting the hydroxy group on the surface to a thiourenium group according to a method known in the art.

If necessary, a protecting group that is generally used for peptide synthesis and the like may be introduced during the production process.

As a material for hydrogel, the polyionic dendrimer of the invention that is produced as above may be used as it is in solution state. Alternatively, it may be dried and then used as a material for hydrogel.

It is preferable that the clay minerals (i.e., clay) that are used as a material for the hydrogel of the invention have a nano sheet structure, but it is not limited thereto. Preferred examples of the clay minerals (i.e., clay) include water-swellable smectite and layer silicate salt such as mica. More specific examples thereof include montmorillonite, hectorite, saponite, bidelite, mica, synthetic mica, and the like. More preferred examples of the clay minerals (i.e., clay) include hectorite. The clay minerals (i.e., clay) can be used as they are in commercially available form.

The use amount of the clay minerals (i.e., clay) is, per 1 part by weight of the polyionic dendrimer of the invention, 1 to 100 parts by weight, preferably 10 to 100 parts by weight, and more preferably 10 to 50 parts by weight.

The linear polymer having an ionic side chain that is used as a material for the hydrogel of the invention is a linear polymer which has an ionic group in its side chain. Preferred examples of the linear polymer having an ionic side chain include an alkali metal salt of polyacrylic acid or polymethacrylic acid. Preferred examples of the alkali metal salt include a sodium salt. Preferred examples of the polymer include sodium polyacrylate.

Polymerization degree of the polymer is not specifically limited. However, it is preferably 100 to 200000, more preferably 2000 to 100000, and still more preferably 20000 to 100000 or 20000 to 70000. The sodium polyacrylate can be used as it is in its commercially available form.

The use amount of the linear polymer having an ionic side chain is, per 1 part by weight of the polyionic dendrimer of the invention, 0.1 to 10 parts by weight, preferably 0.1 to 5 parts by weight, and more preferably 0.1 to 1 part by weight.

Unlike the conventional production of a crosslinked gel based on covalent bond, the method of producing the hydrogel of the invention does not require any polymerization or crosslinking reaction. It only requires simple mixing of the constitutional components. Specifically, as shown in FIG. 1, by adding sodium polyacrylate (ASAP) (3 mg) and clay nano sheet (100 mg) to water (5 mL), a transparent and viscous liquid is obtained (FIG. 1*b*). Subsequently, the polyionic dendrimer (G3) (7.5 mg) which has the third generation dendron on both terminals is added and stirred. As a result, a hydrogel is formed within three minutes (FIG. 1*c*). Even when sodium polyacrylate is not used, the hydrogel can be easily produced according to the same method as above. For specific production examples thereof, see the Examples given below.

FIG. 1 shows a production example of the hydrogel by self-agglomeration of the invention, including a schematic diagram (upper part of FIG. 1) and a color photo (bottom part of FIG. 1). Specifically, FIG. 1*a* illustrates a state in which the clay nano sheet is mixed in water. FIG. 1*a* is the diagrammatic view of the state in which the clay nano sheet is suspended in water, and its color photo is given underneath the diagram. The photo shows that water is slightly turbid due to the suspension. FIG. 1*b* is the diagrammatic view of the state in which sodium polyacrylate (ASAP) is mixed, and its photo is given underneath the diagram. It shows that sodium polyacrylate (ASAP) is attached to the clay nano sheet, and therefore relieving the suspension state.

Further, FIG. 1*c* illustrates the mixing and gellation of the polyionic dendrimer (G3) having the third generation dendrons on both terminals. Corresponding photo is given in the bottom part. In order to clearly show the gelled state, the bottle is shown upside down in the photo of FIG. 1*c*, and its diagrammatic view corresponds to the diagram of FIG. 1*c*. FIG. 1*c* illustrates that the clay nano sheets which have been separately present are gellified by polyionic dendrimer (G3).

Figure 2:
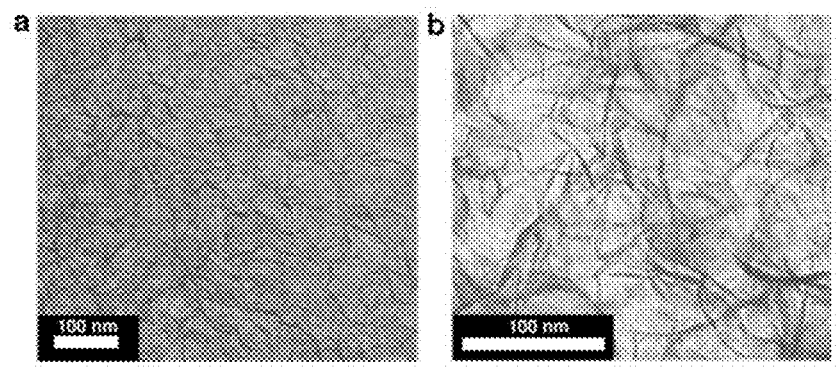
FIG. 2 illustrates the transmission type electron microscopy image of 2% G3-Clay-ASAP hydrogel of the invention.

FIG. 2 illustrates the transmission type electron microscopy image of the 2% G3-Clay-ASAP hydrogel (i.e., hydrogel obtained by using polyionic dendrimer (G3), clay nano sheet (trade name: LAPONITE XLG, manufactured by Rockwood Additives Limited) and sodium polyacrylate (ASAP)) produced in Example 13. It is recognized that the clay nano sheets are linked to each other via the polymer dendronized both terminals thereof so that they are entangled with each other and present in a homogeneously dispersed state.

Figure 3:
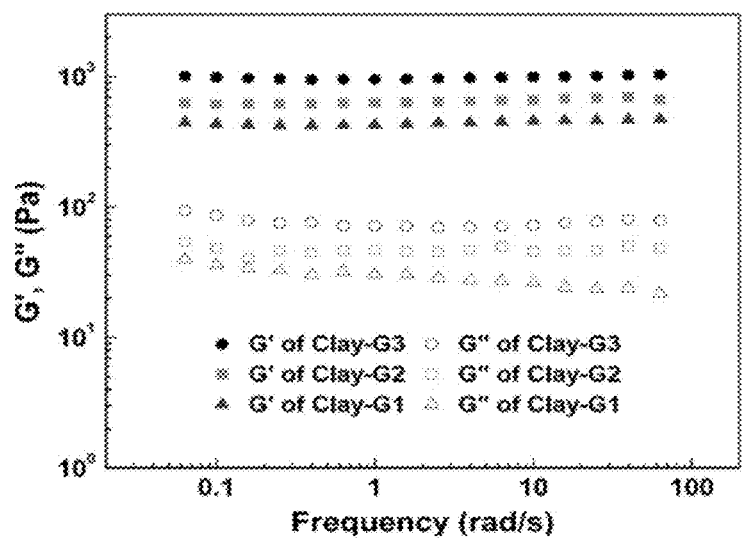
FIG. 3 is a graph which illustrates the results of dynamic viscoelasticity measurement of Clay-G1, Clay-G2, and Clay-G3, that are the hydrogels of the invention.

FIG. 3 illustrates the results of dynamic viscoelasticity measurement of each of Clay-G1, Clay-G2, and Clay-G3 hydrogels, that are produced in Example 9, Example 10, and Example 11, by using ARES-RFS rheometer (manufactured by TA INSTRUMENTS) equipped with a 25 mm parallel disc under the constant strain condition ($\gamma=1\%$). The vertical axis of FIG. 3 represents storage modulus (G') and loss modulus (G") (Pa) and the horizontal axis represents frequency (rad/sec). In FIG. 3, the filled circle (●) represents the frequency distribution of the storage modulus (G') of Clay-G3 hydrogel, the filled square (■) represents the frequency distribution of the storage modulus (G') of Clay-G2 hydrogel, and the filled triangle (▲) represents the frequency distribution of the storage modulus (G') of Clay-G1 hydrogel. The empty circle (○) represents the frequency distribution of the loss modulus (G") of Clay-G3 hydrogel, the empty square (□) represents the frequency distribution of the loss modulus (G") of Clay-G2 hydrogel, and the empty triangle (△) represents the frequency distribution of the loss modulus (G") of Clay-G1 hydrogel.

As a result, it was found that the storage modulus (G') and loss modulus (G") of the hydrogels have a plateau region which does not depend on the frequency. And in the plateau region, G' is bigger than G" (G'>G") and a gel characteristic of a quasi solid state is exhibited. The G' which indicates the strength of the hydrogel increased in accordance with the increase in generation number of the dendron even when the core having the dendrons at both terminals thereof, that is used for the production of the hydrogel, has the same guanidine cation concentration in the dendron of polyethylene glycol, and therefore the effect of the dendron is shown.

Figure 4:
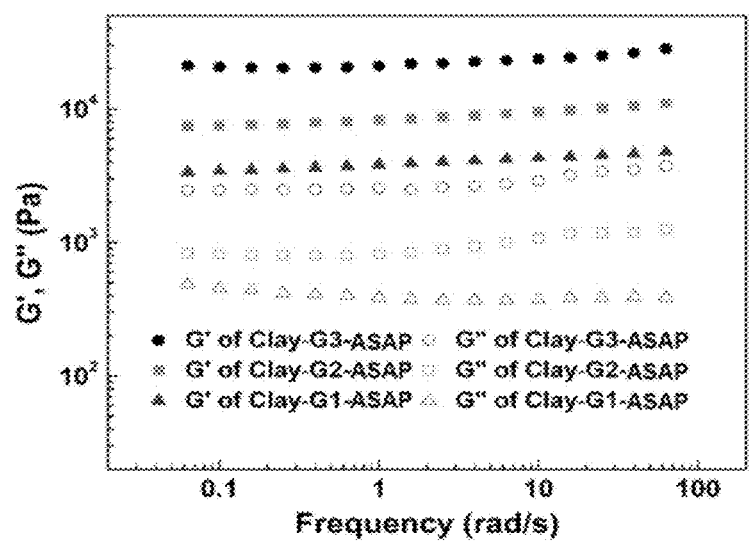
FIG. 4 is a graph which illustrates the results of dynamic viscoelasticity measurement of Clay-G1-ASAP, Clay-G2-ASAP, Clay-G3-ASAP, that are the hydrogels of the invention.

FIG. 4 illustrates the results of dynamic viscoelasticity measurement of each of Clay-G1-ASAP, Clay-G2-ASAP, and Clay-G3-ASAP hydrogels having anionic polymer that are produced in Example 17, Example 18, and Example 19, by using ARES-RFS rheometer (manufactured by TA INSTRUMENTS) equipped with a 25 mm parallel disc under the constant strain condition ($\gamma=1\%$). The vertical axis of FIG. 4 represents storage modulus (G') and loss modulus (G") (Pa) and the horizontal axis represents frequency (rad/sec). In FIG. 4, the filled circle (●) represents the frequency distribution of the storage modulus (G') of Clay-G3-ASAP hydrogel, the filled square (■) represents the frequency distribution of the storage modulus (G') of Clay-G2-ASAP hydrogel, and the filled triangle (▲) represents the frequency distribution of the storage modulus (G') of Clay-G1-ASAP hydrogel. The empty circle (○) represents the frequency distribution of the loss modulus (G") of Clay-G3-ASAP hydrogel, the empty square (□) represents the frequency distribution of the loss modulus (G") of Clay-G2-ASAP hydrogel, and the empty triangle (△) represents the frequency distribution of the loss modulus (G") of Clay-G1-ASAP hydrogel.

As a result, it was found that the effect of the dendrimer is shown also for the strength of the hydrogels, and at the same time, an increase in the strength (G') of the hydrogel is obtained according to the addition of anionic polymers.

Figure 5:
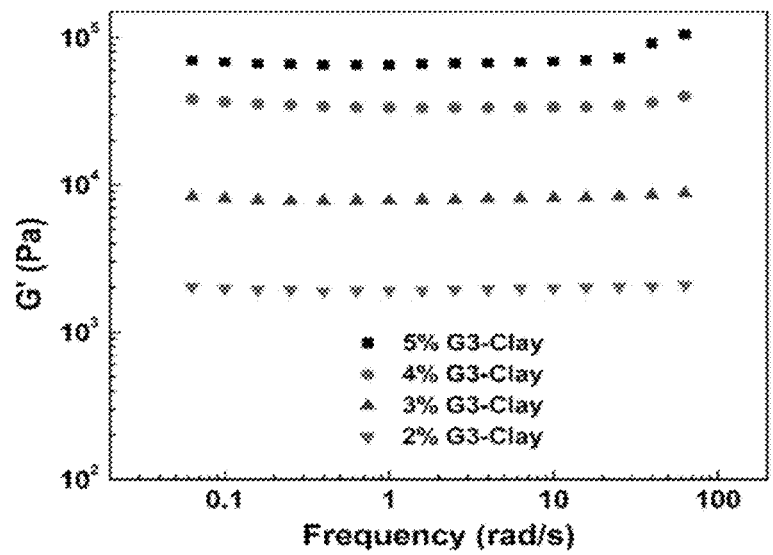
FIG. 5 is a graph which illustrates the effect of the clay nano sheet on the storage modulus of G3-Clay that is the hydrogel of the invention.

FIG. 5 illustrates the results of dynamic viscoelasticity measurement of each of 2% G3-Clay, 3% G3-Clay, 4% G3-Clay, and 5% G3-Clay hydrogels, that are produced in Examples 5 to 8, by using ARES-RFS rheometer (manufactured by TA INSTRUMENTS) equipped with a 25 mm parallel disc under the constant strain condition ($\gamma=1\%$). The vertical axis of FIG. 5 represents storage modulus (G') (Pa) and the horizontal axis represents frequency (rad/sec). In FIG. 5, the filled square (■) represents the frequency distribution of the storage modulus (G') of 5% G3-Clay hydrogel, the filled circle (●) represents the frequency distribution of the storage modulus (G') of 4% G3-Clay hydrogel, the filled triangle (▲) represents the frequency distribution of the storage modulus (G') of 3% G3-Clay hydrogel, and the filled inverted triangle (▼) represents the frequency distribution of the storage modulus (G') of 2% G3-Clay hydrogel.

As a result, it was found that the strength (G') of the hydrogels increases in accordance with the concentration increase of the clay nano sheet, and it is as high as 0.1 MPa for 5% G3-Clay.

Figure 6:
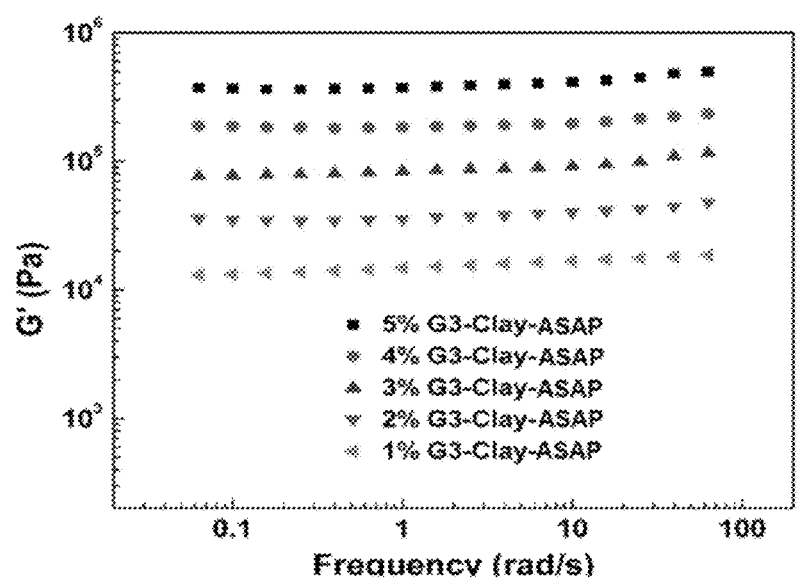
FIG. 6 is a graph which illustrates the effect of the clay nano sheet on the storage modulus of G3-Clay-ASAP that is the hydrogel of the invention.

FIG. 6 illustrates the results of dynamic viscoelasticity measurement of each of 1% G3-Clay-ASAP, 2% G3-Clay-ASAP, 3% G3-Clay-ASAP, 4% G3-Clay-ASAP, and 5% G3-Clay-ASAP hydrogels, that are produced in Example 12 to Example 16, by using ARES-RFS rheometer (manufactured by TA INSTRUMENTS) equipped with a 25 mm parallel disc under the constant strain condition ($\gamma=1\%$). The vertical axis of FIG. 6 represents storage modulus (G') (Pa) and the horizontal axis represents frequency (rad/sec). In FIG. 6, the filled square (■) represents the frequency distribution of the storage modulus (G') of 5% G3-Clay-ASAP hydrogel, the filled circle (●) represents the frequency distribution of the storage modulus (G') of 4% G3-Clay-ASAP hydrogel, the filled triangle (▲) represents the frequency distribution of the storage modulus (G') of 3% G3-Clay- ASAP hydrogel, the filled inverted triangle (▼) represents the frequency distribution of the storage modulus (G') of 2% G3-Clay-ASAP hydrogel, and the filled left pointed triangle represents the frequency distribution of the storage modulus (G') of 1% G3-Clay-ASAP hydrogel.

As a result, it was found that the strength (G') of the hydrogels increases in accordance with the concentration increase of the clay nano sheet, and it is as high as 0.5 MPa for 5% G3-Clay-ASAP.

Figure 7:
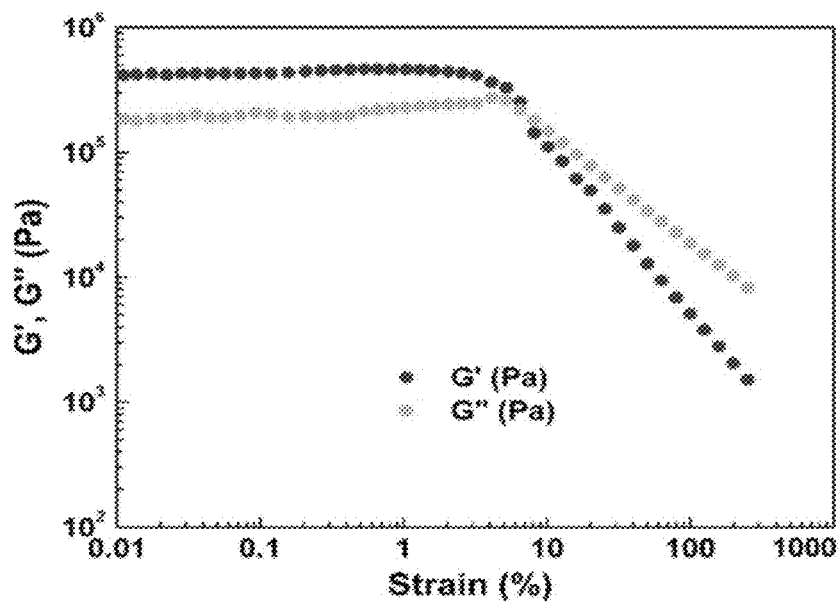
FIG. 7 is a graph which illustrates the strain dependency of the dynamic viscoelasticity measurement of 5% G3-Clay-ASAP that is the hydrogel of the invention.

FIG. 7 illustrates the results of dynamic viscoelasticity measurement of 5% G3-Clay-ASAP hydrogel, that is produced in Example 16, by using ARES-RFS rheometer (manufactured by TA INSTRUMENTS) equipped with a 25 mm parallel disc under the constant strain condition ($\gamma=1\%$). The vertical axis of FIG. 7 represents storage modulus (G') and loss modulus (G") (Pa) and the horizontal axis represents frequency (rad/sec). In FIG. 7, the filled circle (●) represents the frequency distribution of the storage modulus (G') of 5% G3-Clay-ASAP hydrogel and the gray circle (○) represents the frequency distribution of the loss modulus (G") of 5% G3-Clay-ASAP hydrogel.

As a result, it was found that 5% G3-Clay-ASAP is a quasi solid gel which has the storage modulus (G') of 0.5 Mpa under low strain condition. However, G' starts to rapidly decrease with the strain exceeding the critical strain ($\gamma=9\%$), and as a result the gel is disrupted to yield a quasi liquid state.

Figure 8:
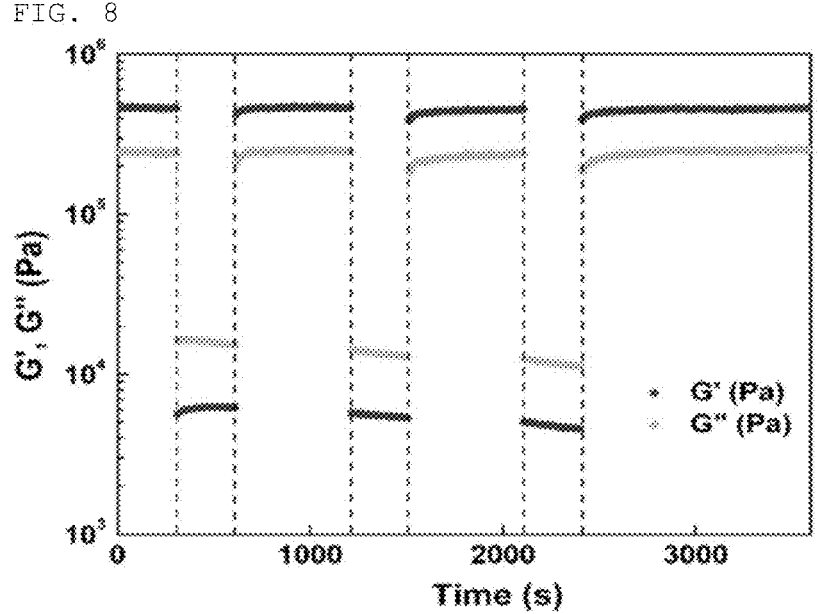
FIG. 8 is a graph which illustrates the result of the measurement of high speed viscoelasticity recovery property of 5% G3-Clay-ASAP that is the hydrogel of the invention.

FIG. 8 illustrates the results of dynamic viscoelasticity measurement of 5% G3-Clay-ASAP hydrogel, that is produced in Example 16, by using ARES-RFS rheometer (manufactured by TA INSTRUMENTS) equipped with a 25 mm parallel disc. The vertical axis of FIG. 8 represents storage modulus (G') and loss modulus (G") (Pa) and the horizontal axis represents the time (sec). In FIG. 8, the dark solid line (i.e., dark navy line in the original drawing) represents the storage modulus (G') of 5% G3-Clay-ASAP hydrogel and the light solid line (i.e., sky blue line in the original drawing) represents the loss modulus (G") of 5% G3-Clay-ASAP hydrogel.

As a result, under the condition including frequency ($\omega$) of 6 rad/s (1 Hz) and strain ($\gamma$) of 0.1%, the storage modulus (G') was about 0.5 MPa, indicating a quasi solid property with the loss tangent (tan $\delta$=G"/G') value of about 0.4 to 0.5 (FIG. 8). When 100% strain was applied to the gel while maintaining the same frequency of 6 rad/s, the storage modulus (G') was deceased to about 5 KPa, yielding a quasi liquid property with the loss tangent (tan $\delta$=G"/G') value of 3 to 4. Further, when 100% strain load is continuously applied for 300 seconds and then immediately the dynamic viscoelasticity is measured after adjusting the strain back to 0.1%, the storage modulus (G') was immediately restored to 0.5 MPa. This high speed return behavior has a repeating characteristic so that the high speed return behavior was not impaired even after continuously repeating three times the cycle of low strain load (0.1%) and high strain load (100%). From such result, it was found that the hydrogel of the invention has a specific high speed return behavior. Although a hydrogel with the same behavior has been reported before, under low strain condition, the hydrogel of the invention has storage modulus (0.5 MPa) that is one digit higher than that of the oligomeric electrolyte hydrogel (Non-patent Document 9), 2 to 3 digits higher than that of copolypeptide hydrogel (Non-patent Document 10), and also almost 2 digits higher than that of the hydrogel consisting of an ionic organic compound which contains a quaternary ammonium cation formed of a heterocyclic compound such as pyridine (Patent Document 8).

Taken together, it was shown that the hydrogel of the invention has a high self-restoring property.

Figure 9:
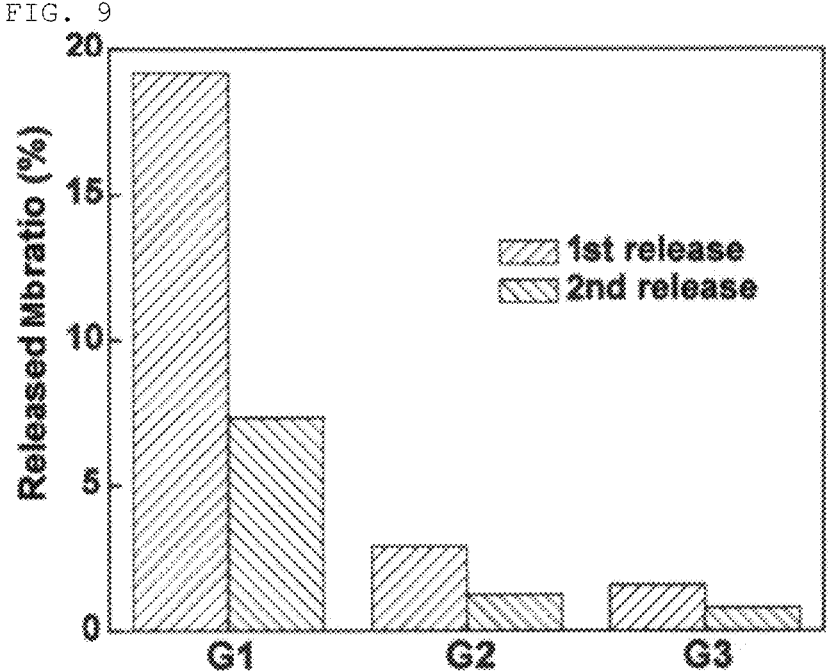
FIG. 9 is a graph which illustrates the result of the ratio of released myoglobin that has been introduced to the hydrogel of the invention.

FIG. 9 includes a graph showing the released myoglobin ratio ($1^{st}$ release) which is obtained by centrifuging each of the myoglobin (Mb)-containing G3-Clay-Mb, G1-Clay-Mb, and G2-Clay-Mb hydrogels, that are produced in Example 27, Example 28, and Example 29, at 15,000 rpm and analyzing the isolated myoglobin concentration in water based on the absorption of the soret band at 405 nm, and the second released myoglobin ratio ($2^{nd}$ release) which is obtained by treating the dehydrated hydrogel with water, centrifuging the gel again at 15,000 rpm, and obtaining the isolated myoglobin concentration in water. The vertical axis of FIG. 9 represents released myoglobin ratio (%). The horizontal axis represents, from the left side, G1-Clay-Mb (G1), G2-Clay-Mb (G2), and G3-Clay-Mb (G3), respectively. For each hydrogel, the left bar indicates the result of the $1^{st}$ release and the right bar indicates the result of the $2^{nd}$ release.

As a result, it was found that the amount of released myoglobin is very small and the released ratio is dramatically decreased as the generation of dendron group in the polymer which has dendron groups at both terminals thereof increases.

Figure 10:
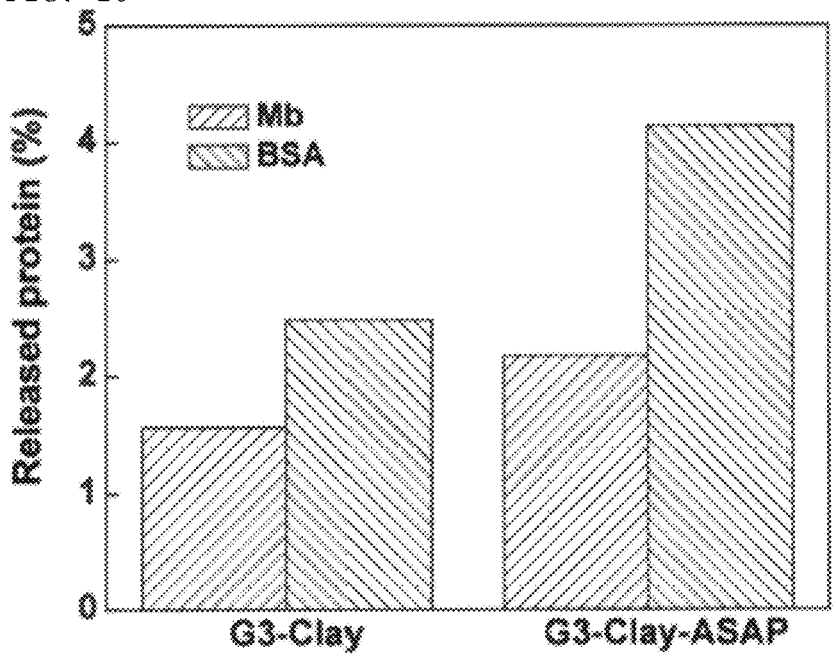
FIG. 10 is a graph which illustrates the result of the ratio of released myoglobin and albumin that have been introduced to the hydrogel of the invention.

FIG. 10 includes a graph showing the released myoglobin or albumin ratio which is obtained by centrifuging each of G3-Clay-Mb, G3-Clay-BSA, G3-Clay-ASAP-Mb, and G3-Clay-ASAP-BSA hydrogels, that are produced in Example 27, Example 30, Example 31, and Example 32, at 15,000 rpm and analyzing the isolated myoglobin or albumin concentration in water based on the absorption at 405 nm of the soret band or 280 nm. The vertical axis of FIG. 10 represents the released protein ratio (%). The horizontal axis represents, from the left side, G3-Clay and G3-Clay-ASAP, respectively. For each hydrogel, the left bar indicates the result obtained from myoglobin (Mb) and the right bar indicates the result obtained from albumin (BSA).

As a result, it was found that both the released myoglobin ratio and the released albumin ratio were 5% or less.

Figure 11:
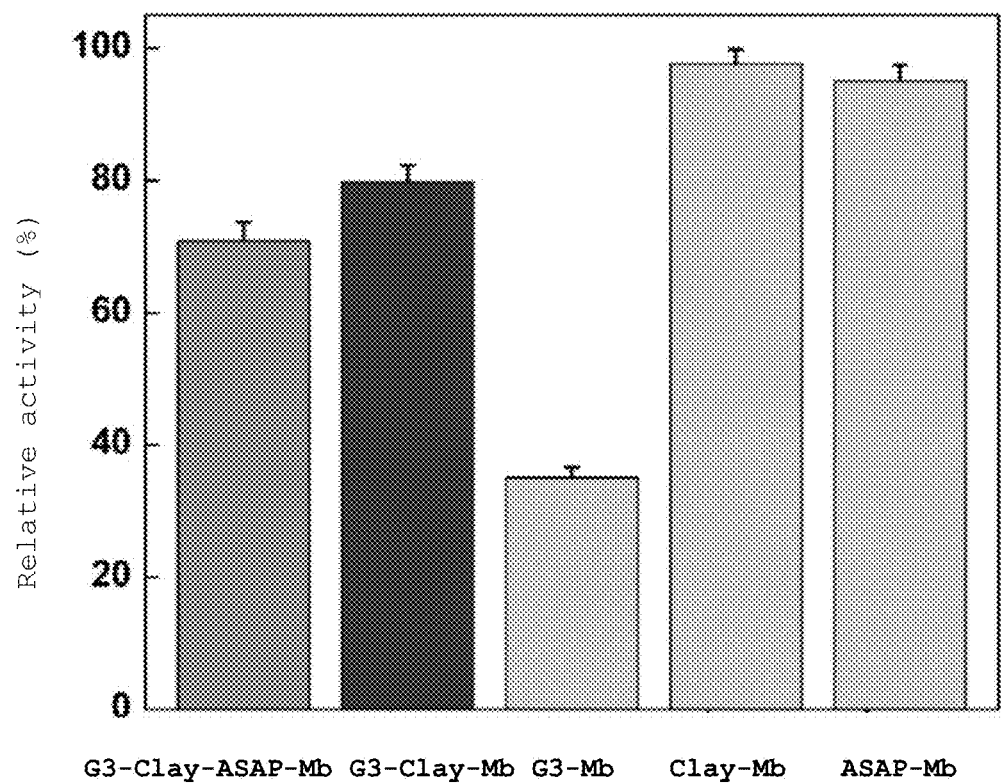
FIG. 11 is a graph which illustrates the results of measuring the activity of myoglobin which has been introduced to the hydrogel of the invention.

FIG. 11 is a graph which illustrates the results of examining the activity of myoglobin by using G3-Clay-Mb and G3-Clay-ASAP-Mb hydrogels of Example 27 and Example 31 with the myoglobin concentration of 0.5 µM. For the comparison, the same measurement was carried out for each of Clay-Mb, ASAP-Mb, and G3-Mb and the results are also included. The vertical axis of FIG. 11 represents the relative activity of myoglobin (%). The horizontal axis represents, from the left side, G3-Clay-ASAP-Mb, G3-Clay-Mb, G3-Mb, Clay-Mb, and ASAP-Mb, respectively.

As a result, it was found that activity of the myoglobin in the systems of Clay-Mb and ASAP-Mb is 98% or 96% of the activity of free myoglobin, respectively and thus the clay nano sheet and ASAP have no effect on the activity of myoglobin. Meanwhile, the activity of the myoglobin in the G3-Mb system was only 35% of the activity of free myoglobin. It is believed that such dramatic decrease in myoglobin activity in this system is due to the presence of a great excess amount of the guanidine group (500 µM) in G3 compared to the myoglobin (5 µM), showing a great effect of the guanidine group on the myoglobin activity.

In this regard, as the most of the guanidine group in the systems of G3-Clay-Mb and G3-Clay-ASAP-Mb are present on the surface of the clay nano sheet, the above-mentioned effect becomes very small in these systems. In other words, it was found that, although the hydrogel of the invention contains many cationic groups, they are present on the surface of the clay nano sheet, and therefore have not much effect on the activity of a physiologically active protein.

Further, the myoglobin activity in the G3-Clay-Mb system is slightly higher than that of G3-Clay-ASAP-Mb, and it is believed to be based on the reason that the strength of the G3-Clay-ASAP gel is stronger than that of G3-Clay and the structure of the hydrogel is slightly weaker in G3-Clay-Mb compared to in G3-Clay-ASAP-Mb, and therefore diffusion can occur more easily in G3-Clay-Mb.

Figure 12:
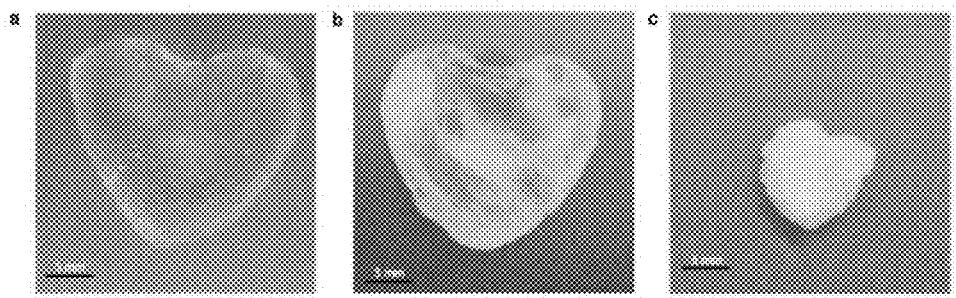
FIG. 12 is a color photo which illustrates the shape-retaining property of the hydrogel of the invention.

FIG. 12 is a color photo which illustrates the shape of 5% G3-Clay-ASAP hydrogel, wherein the hydrogel has been prepared to have a heart shape, and then either immersed in tetrahydrofuran (THF) or dried. FIG. 12a represents the G3-Clay-ASAP hydrogel, FIG. 12b represents the gel obtained after the immersion in THF, and FIG. 12c represents the gel obtained after the drying.

In general, a physically crosslinked hydrogel loses its shape when it is immersed in THF. However, the hydrogel of the invention maintained the heart shape as shown in FIG. 12b. Further, although the gel was shrunken all around when it is dried, the overall heart shape was maintained as shown in FIG. 12c. Further, when the dried gel is added into water, it is restored to the heart-shape gel shown in FIG. 12a.

As shown in the above, the invention provides a novel material for hydrogel containing a hydrophilic linear polymer such as polyalkylene glycol in the core part and polyester dendrons attached to both terminals of the linear polymer so that cationic groups such as guanidine groups are present on the surfaces of the dendrons, and clay minerals (i.e., clay) with a nano sheet structure.

The hydrogel of the invention, which is a composite resulting from the binding of the polyionic dendrimer of the invention to the surface of the clay minerals (i.e., clay) with a nano sheet structure via electrostatic interaction and hydrogen bond, and the like, is characterized in that it can contain water at high water content (i.e., at least 94%), is a transparent gel with high strength, and has a self-restoring property, a shape-retaining property, and a characteristic of maintaining behavior of a protein such as a protein having a physiologically activity or an enzymatically activity without modifying the behavior of the protein.

As such, the hydrogel of the invention is very useful not only for the conventional use of hydrogel but also for various industrial fields including pharmaceuticals, food products, cosmetics, hygienic products, and the like.

Herein below, the invention is explained in greater detail in view of the Examples. However, the invention is not limited by the Examples.

Example 1

G1-OH, G2-OH, and G3-OH were produced in accordance with the reaction scheme shown below.

[Chemical Formula 5]

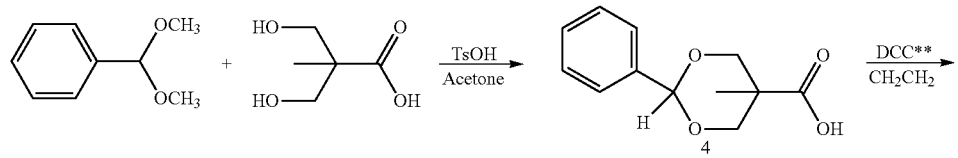

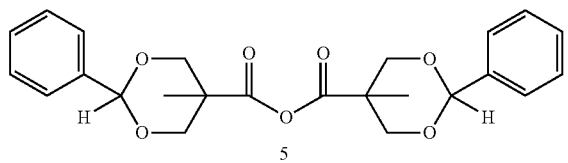

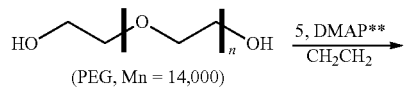

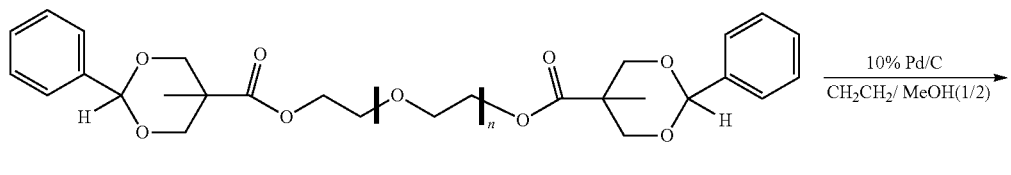

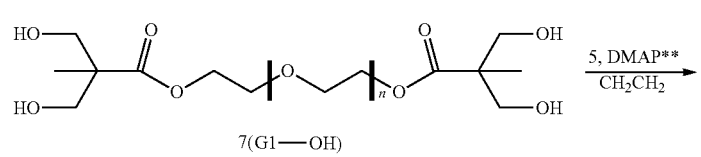

21
-continued
22
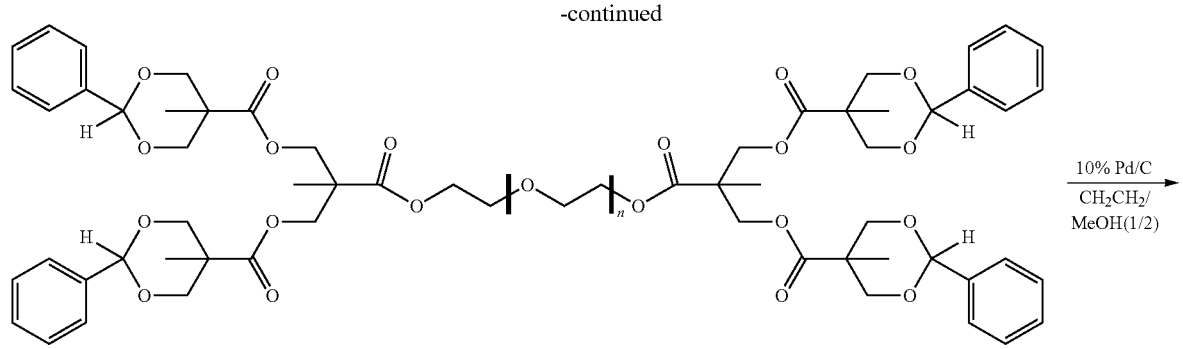
10% Pd/C
CH₂CH₂/
MeOH(1/2) →
8
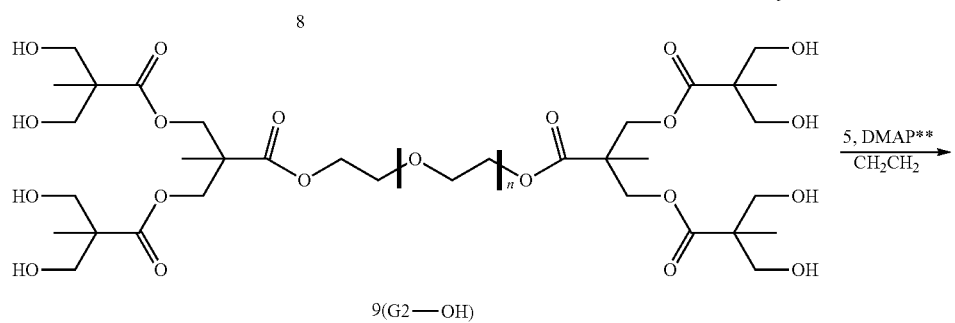
5, DMAP**
CH₂CH₂ →
9(G2—OH)
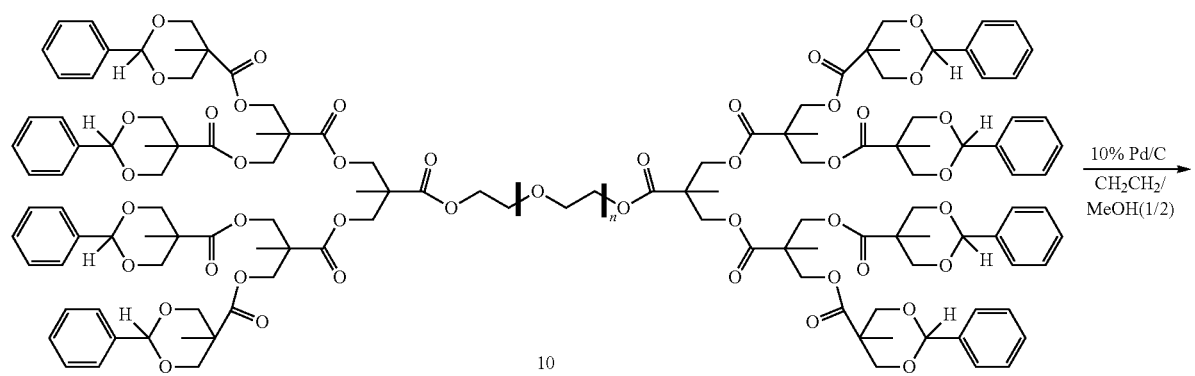
10% Pd/C
CH₂CH₂/
MeOH(1/2) →
10
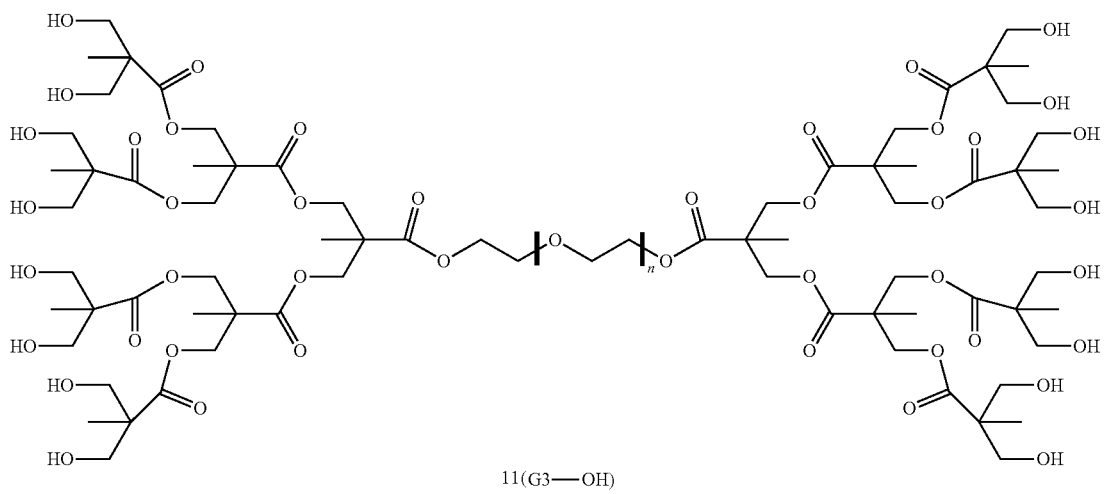
11(G3—OH)
*DCC: N,N′-dicyclohexylcarbo-diimide
**DMAP: 4-(dimethylamino)pyridine Compound 7 (G1-OH), that is a bisdendrimer having a hydroxy group as the surface, a polyester group as the branched chain, and polyethylene glycol group as the core, and its second generation compound and third generation compound, i.e., Compound 9 (G2-OH) and Compound 11 (G3-OH), were produced according to the method described in the Document (Non-patent Document 8; H. Ihre, O. L. Padilla De Jesus, J. M. J. Frechet, J. Am. Chem. Soc. 123, 5908 (2001)).

NMR and MS Data of Compound 7 (G1-OH):

$^1$H-NMR (270 MHz, CDCl$_3$) δ:

1.09 (s, 6), 3.64 (bs, ~1200), 4.32 (t, 4, J=5.0).

MALDI-TOF-MS: [M]$^+$=10879.

NMR and MS Data of Compound 9 (G2-OH):

$^1$H-NMR (270 MHz, CDCl$_3$) δ:

1.05 (s, 12), 1.29 (s, 6), 3.36 (t, 10, J=4.8), 3.64 (bs, ~1200), 4.32 (m, 8), 4.40 (d, 4, J=11.1).

MALDI-TOF-MS: [M]$^+$=11476.

NMR and MS Data of Compound 11 (G3-OH):

$^1$H-NMR (270 MHz, CDCl$_3$) δ:

1.05 (s, 24), 1.28 (s, 18), 3.28 (t, 5, J=5.8), 3.35 (t, 5, J=5.8), 3.50 (t, 6, J=5.8), 3.64 (bs, ~1200), 3.78 (m, 25), 4.28 (m, 20).

MALDI-TOF-MS: [M]$^+$=12620.

Example 2

G1 was produced in accordance with the reaction scheme shown below.

[Chemical Formula 6]

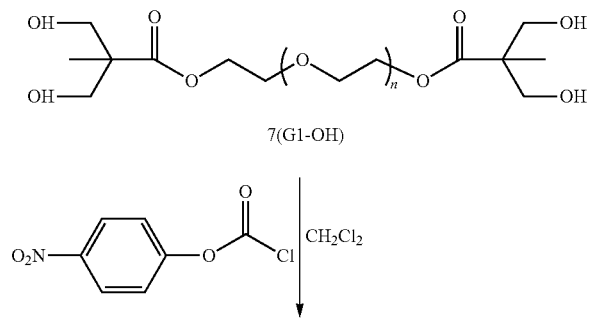

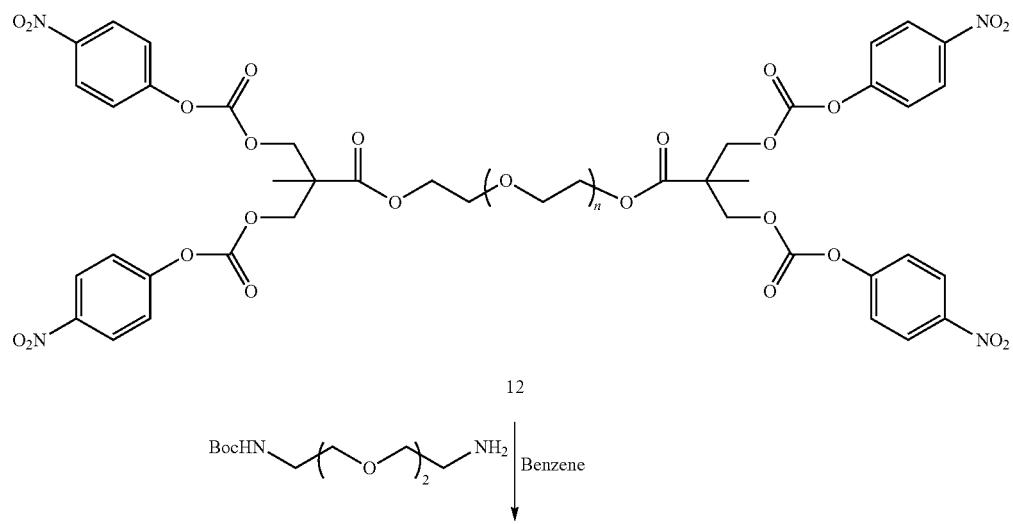

25 26
-continued
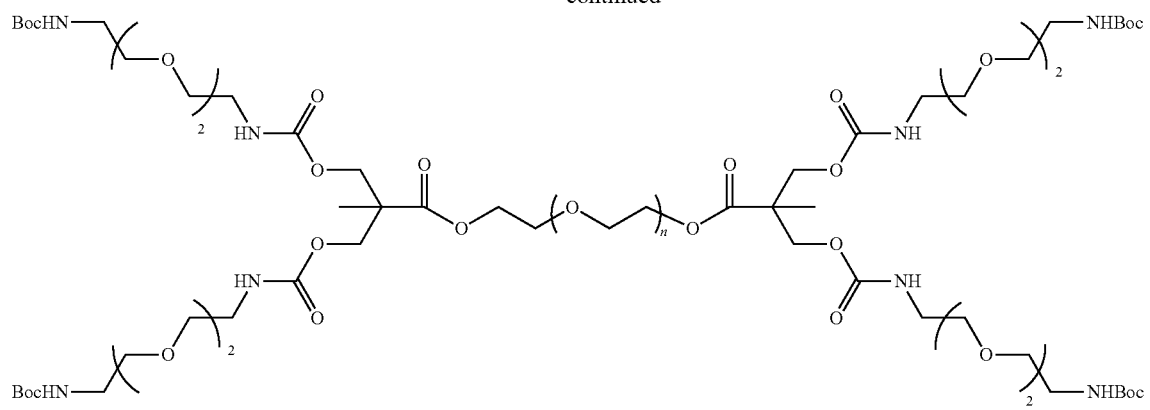
13(G1-NH(Boc))
$\Big| \begin{array}{c} CH_2Cl_2:TFA \\ 1:1 \end{array}$
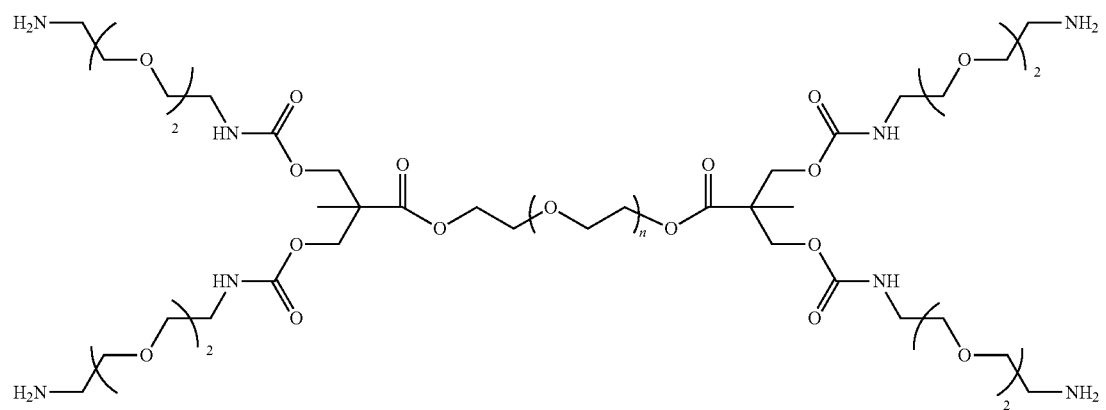
14
$\Big| \begin{array}{c} CH_2Cl_2 \\ Et_3N \end{array}$ (BocHN-C(=NTf)-NHBoc)

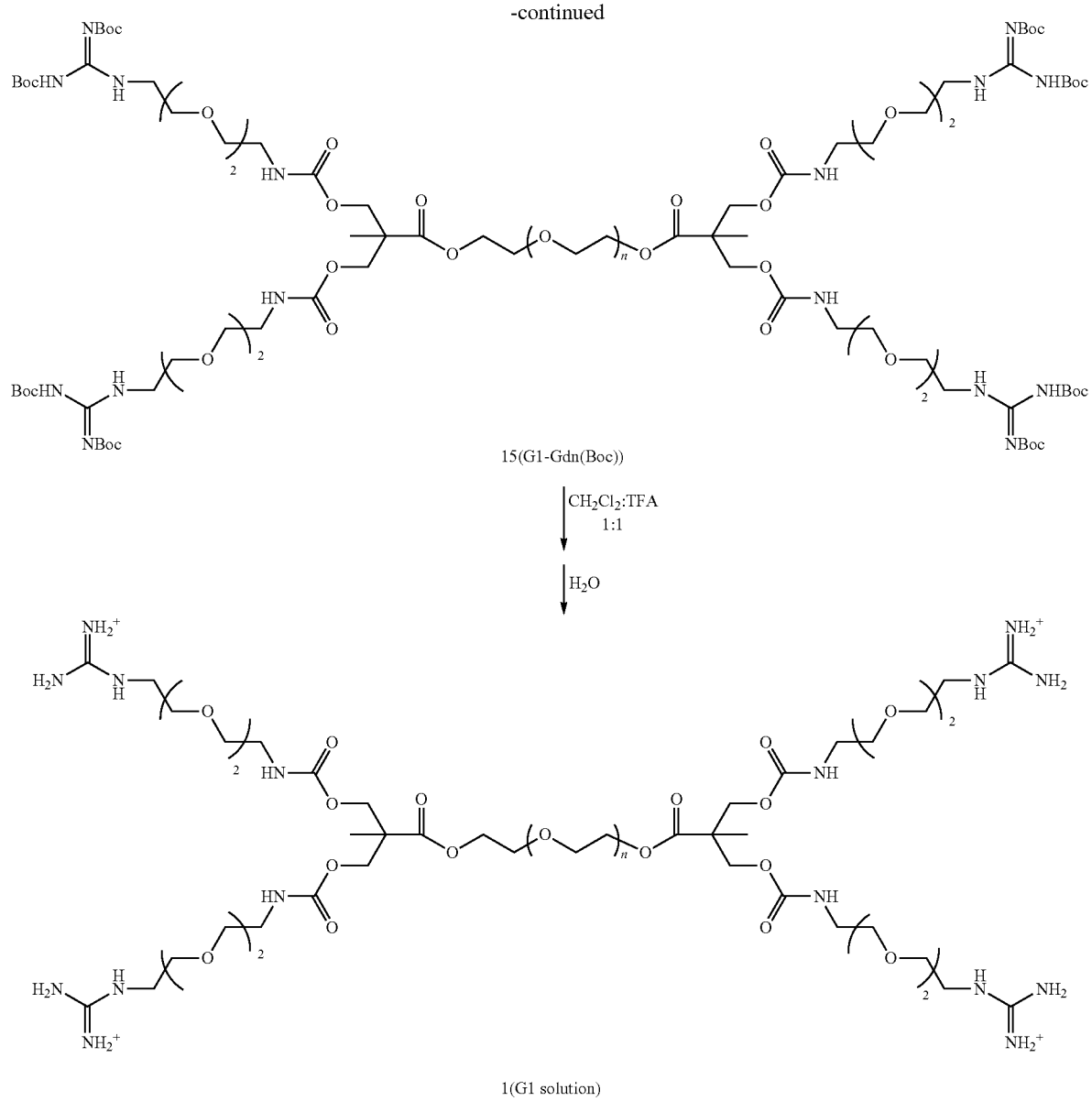

15(G1-Gdn(Boc))

1(G1 solution)

(1) Production of Compound 13 (G1-NH(Boc))

1.0 g (0.09 mmol, 1 eq.) of Compound 7 (G1-OH) was dissolved in 5.0 mL of dichloromethane ($CH_2Cl_2$), added with 0.25 mL of pyridine and 0.40 g (2.0 mmol, 22 eq.) of 4-nitrophenylchloroformate, and then reacted by stirring at room temperature for 22 hours. The reaction solution was poured in diethyl ether to precipitate Compound 12, which was then purified. Compound 12 was dissolved in 6.0 mL benzene, added with 0.07 g (0.51 mmol, 5.7 eq.) of 4-(dimethylamino)pyridine (DMAP) and 0.35 g of tert-butyl 2-(2-(2-aminoethoxy)ethoxy)ethylcarbamate, and then reacted by stirring at room temperature for 12 hours. The reaction solution was poured in diethyl ether to obtain 0.8 g of Compound 13 as a white solid (yield 68%).

$^1$H-NMR (270 MHz, $CDCl_2$) δ:
1.20 (s, 6), 1.04 (s, 6), 1.42 (s, 36),
3.64 (bs, ~1200), 4.19 (t, 8, J=5.0).
MALDI-TOF-MS: $[M]^+$=11684.

(2) Production of Compound 15 (G1-Gdn(Boc))

0.3 g of Compound 13 was dissolved in 1 mL of a mixed solvent of trifluoroacetic acid (TFA) and dichloromethane (1:1), and stirred for 5 hours at room temperature to remove the protective group. Subsequently, the reaction solution was poured in diethyl ether to obtain Compound 14 as a precipitate. Thus-obtained Compound 14 was dissolved in 8 mL of dichloromethane, added with 0.50 mL of triethylamine and 50 mg of N,N'-di(tert-butyloxycarbonyl)-N''-trifluoromethane sulfonylguanidine, and then reacted by stirring at room temperature for 8 hours. The reaction solution was poured in diethyl ether to obtain 0.22 g of Compound 15 as a white solid (yield 62%).

$^1$H-NMR (270 MHz, $CDCl_3$) δ:
1.20 (s, 6), 1.48 (s, 72), 3.64 (bs, ~1200),
4.19 (t, 8, J=5.0).
MALDI-TOF-MS: $[M]^+$=11863.

(3) Production of Compound 1 (G1 (Solution))

0.032 g of Compound 15 was dissolved in 0.50 mL of a mixed solvent of trifluoroacetic acid and dichloromethane (1:1), and stirred for 6 hours at room temperature to remove the protective group, therefore obtaining Compound 1 (G1). The reaction was followed by NMR and complete loss of the signal at 1.48 verified the removal of the protective group in Compound 15. The reaction solution was subjected to high vacuum to remove the solvent and the by-products. After adding 1.0 mL of pure water, an aqueous solution of 3% by weight of G1 was used as it is for production of a hydrogel.

Example 3

G2 was produced in accordance with the reaction scheme shown below.

[Chemical Formula 7]

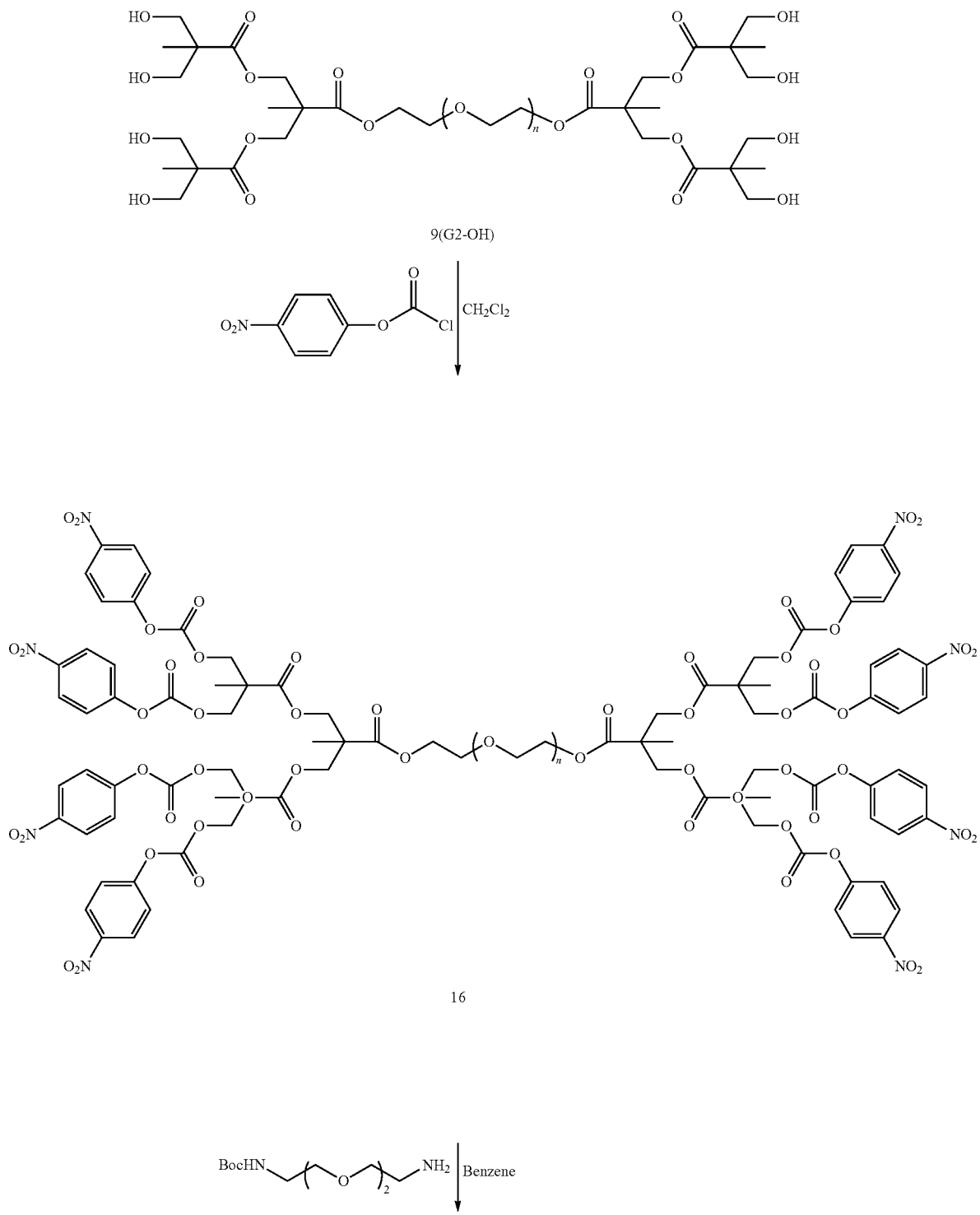

31 32
-continued
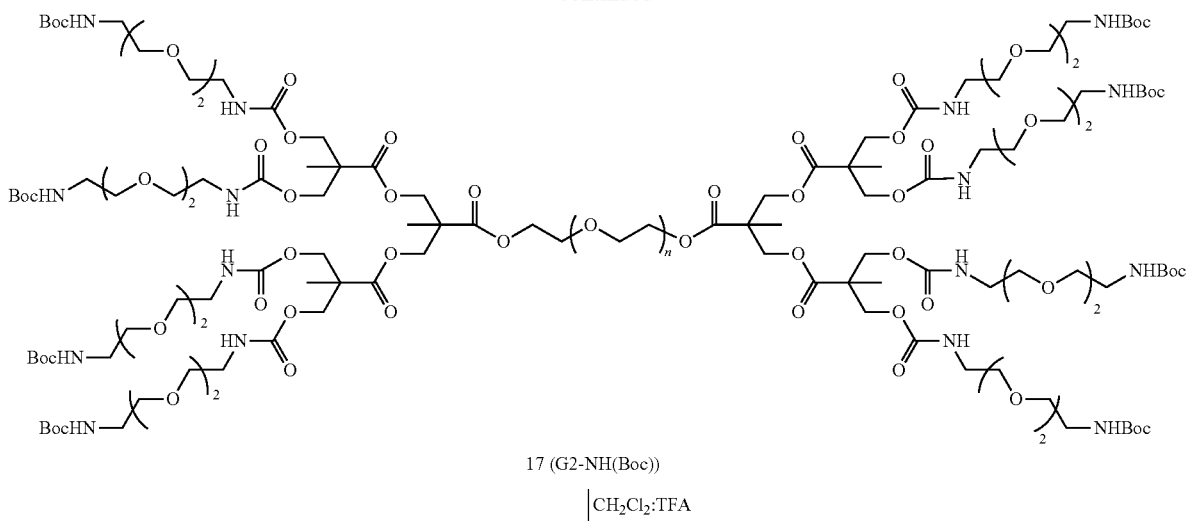
17 (G2-NH(Boc))
CH₂Cl₂:TFA
1:1
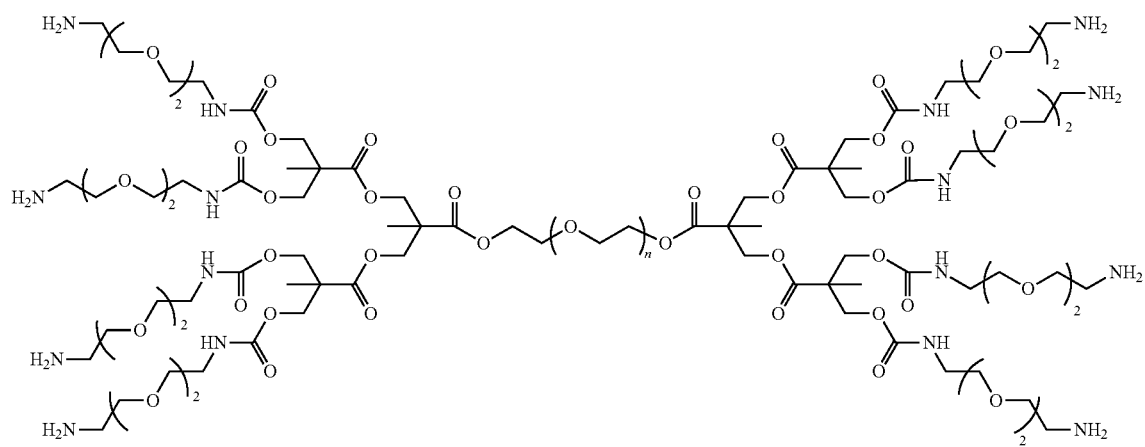
18
BocHN-C(=NTf)-NHBoc
CH₂Cl₂:TFA
1:1

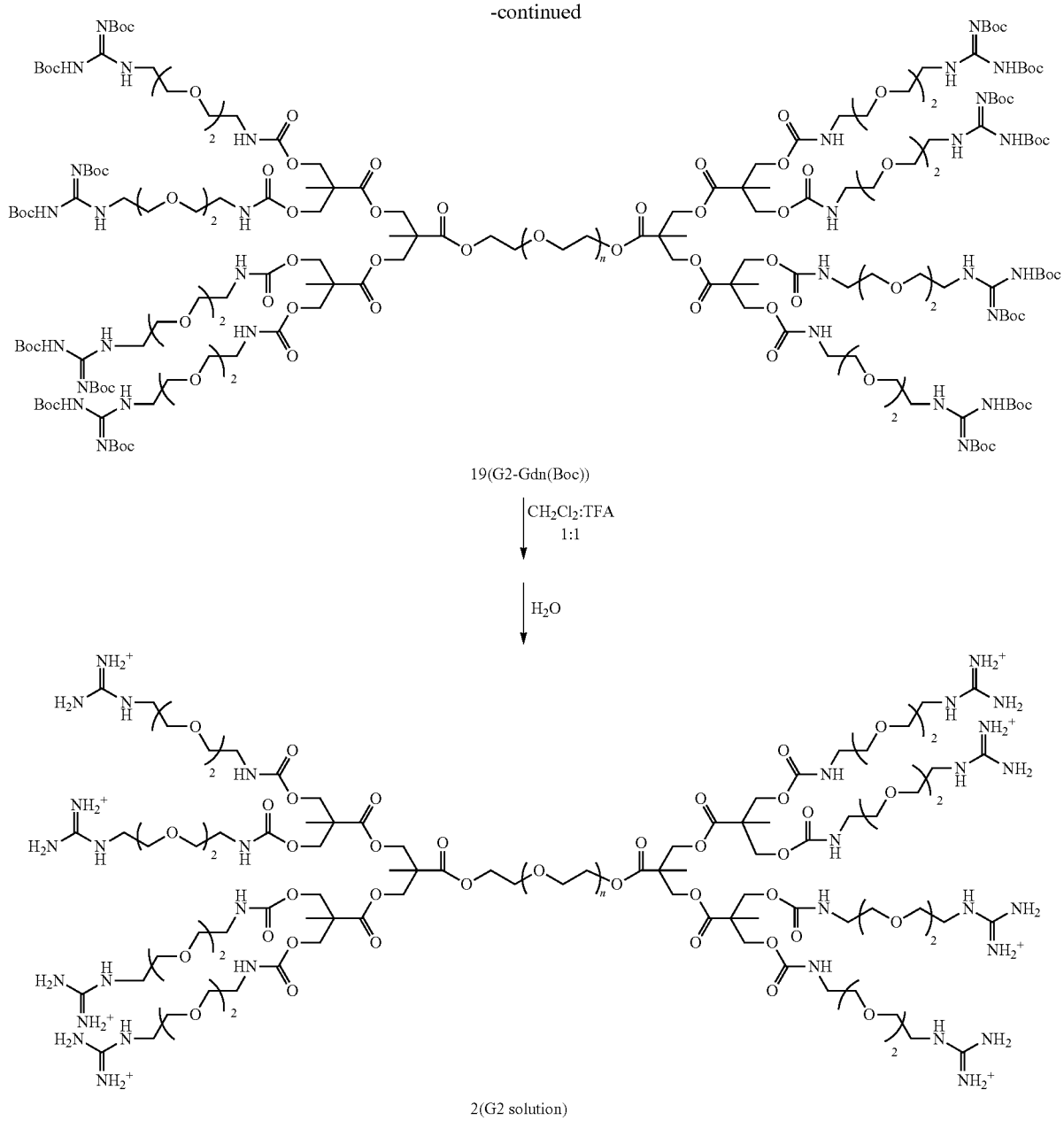

(1) Production of Compound 17 (G2-NH(Boc))

1.0 g (0.09 mmol, 1 eq.) of Compound 9 (G2-OH) was dissolved in 5.0 mL of dichloromethane, added with 0.25 mL of pyridine and 0.80 g (4.0 mmol, 44 eq.) of 4-nitrophenyl-chloroformate, and then reacted by stirring at room temperature for 12 hours. The reaction solution was poured in diethyl ether to precipitate Compound 16, which was then purified. Compound 16 was dissolved in 6.0 mL of benzene, added with 0.14 g (1.02 mmol, 11.4 eq.) of 4-(dimethylamino)pyridine (DMAP) and 0.70 g of tert-butyl 2-(2-(2-aminoethoxy)ethoxy)ethylcarbamate, and then reacted by stirring at room temperature for 12 hours. The reaction solution was poured in diethyl ether to obtain 0.71 g of Compound 17 as a white solid (yield 55%).

$^1$H-NMR (270 MHz, CDCl$_3$) δ:
1.17 (s, 12), 1.24 (s, 6), 1.42 (s, 72),
3.64 (bs, ~1200), 4.16 (t, 16, J=5.0)
MALDI-TOF-MS: [M]$^+$=12542.

(2) Production of Compound 19 (G2-Gdn(Boc))

0.3 g of Compound 17 was dissolved in 2 mL of a mixed solvent of trifluoroacetic acid and dichloromethane (1:1), and stirred at room temperature for 5 hours to remove the protective group. Subsequently, the reaction solution was poured in diethyl ether to obtain Compound 18 as a precipitate. Thus-obtained Compound 18 was dissolved in 8.0 mL dichloromethane, added with 1.0 mL of triethylamine and 0.10 g of N,N'-di(tert-butyloxycarbonyl)-N''-trifluoromethane sulfonylguanidine, and then reacted by stirring at room temperature for 8 hours. The reaction solution was poured in diethyl ether to obtain 0.18 g of Compound 19 as a white solid (yield 58%).

$^1$H-NMR (270 MHz, CDCl$_3$) δ:
1.16 (s, 12), 1.24 (s, 6), 1.47 (s, 144),
3.64 (bs, ~1200), 4.16 (t, 16, J=5.0).
MALDI-TOF-MS: [M]$^+$=12896.

(3) Production of Compound 2 (G2 (Solution))

0.034 g of Compound 19 was dissolved in 0.50 mL of a mixed solvent of trifluoroacetic acid and dichloromethane (1:1), and stirred at room temperature for 6 hours to remove the protective group of Compound 19, therefore obtaining Compound 2 (G2). The reaction was followed by NMR and complete loss of the signal at 1.47 verified the removal of the protective group. The reaction solution was subjected to high vacuum to remove the solvent and the by-products. After adding 1.0 mL of pure water, an aqueous solution of 3% by weight of G2 was used as it is for production of a hydrogel.

Example 4

G3 was produced in accordance with the reaction scheme shown below.

[Chemical Formula 8]
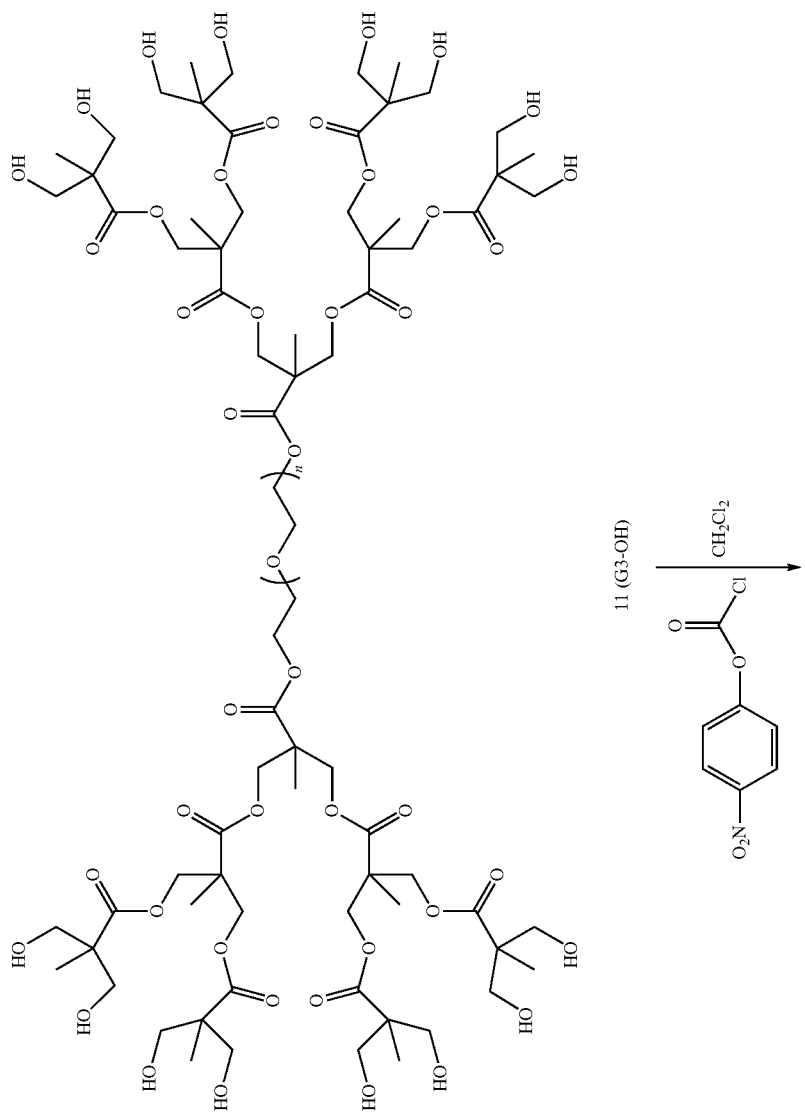

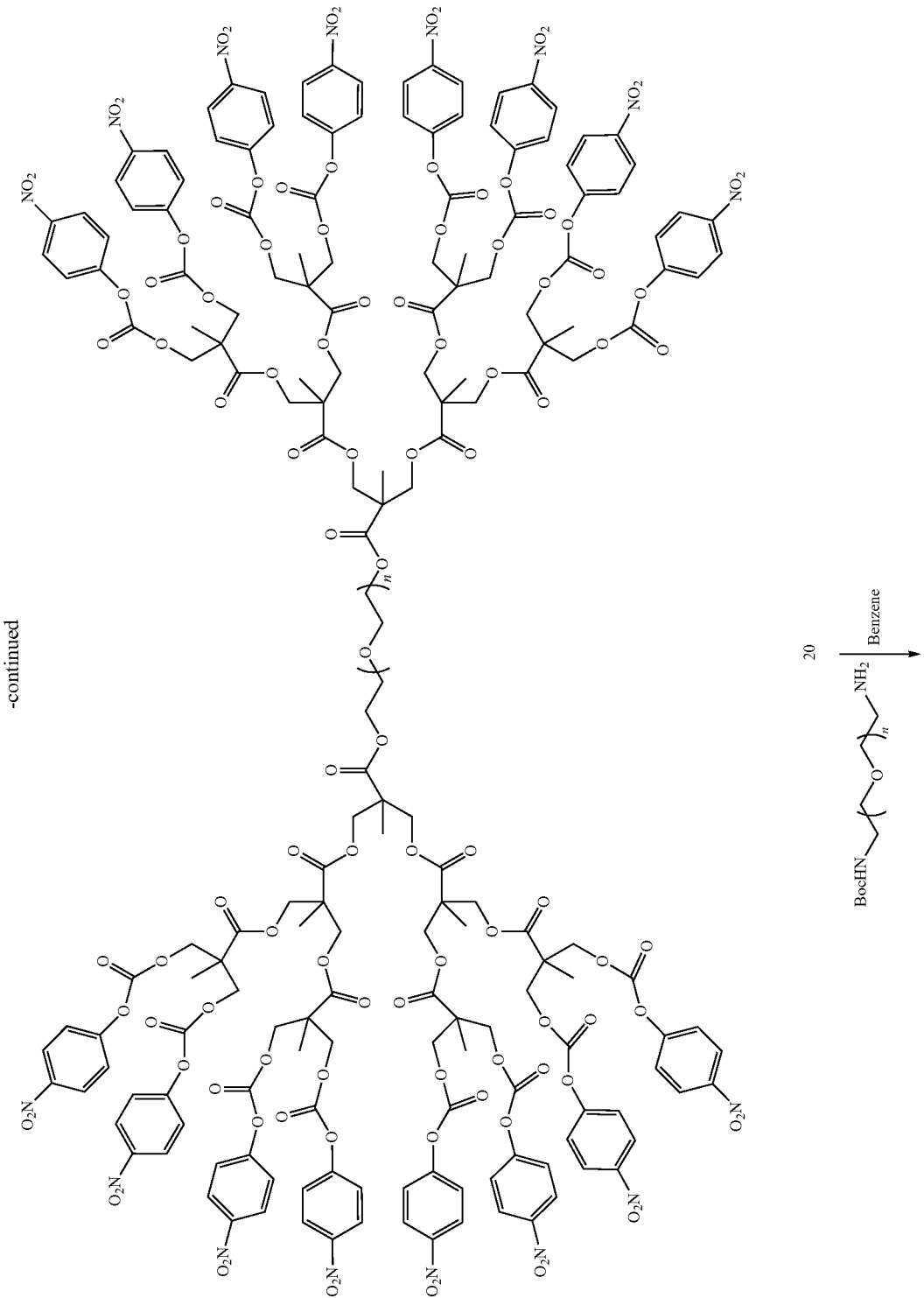

-continued
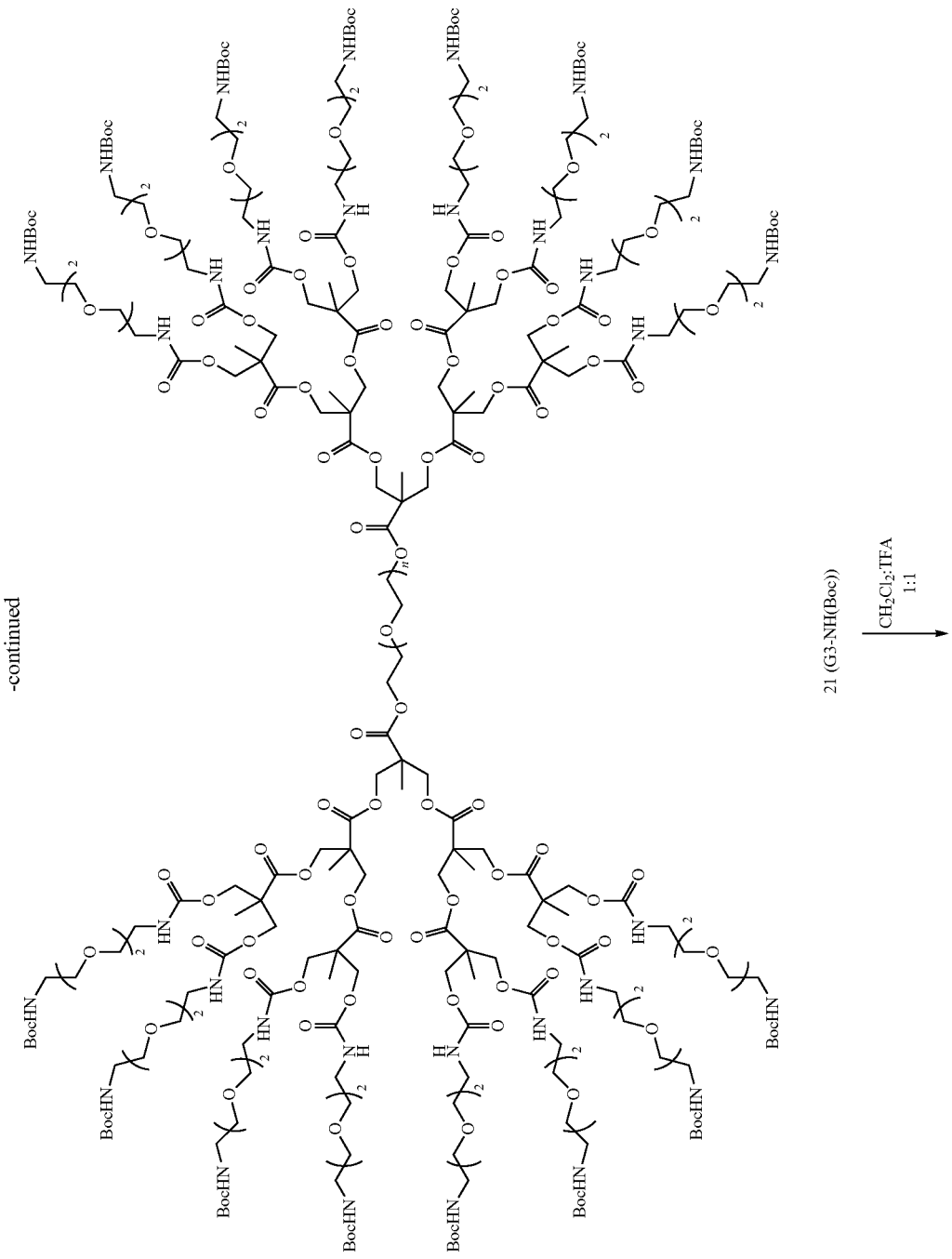
21 (G3-NH(Boc))
$\xrightarrow{\text{CH}_2\text{Cl}_2:\text{TFA} \\ 1:1}$

[Chemical Formula 9]
-continued
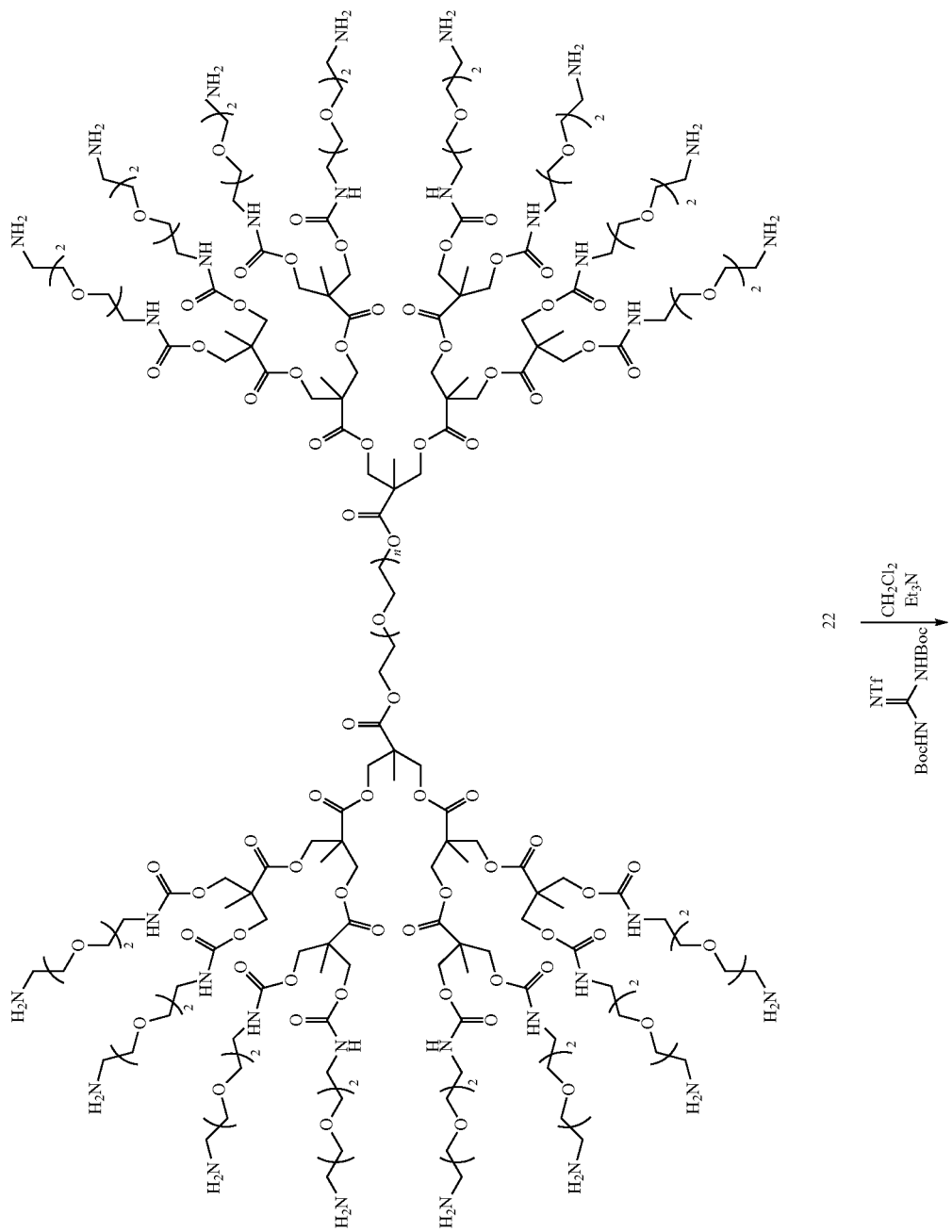

-continued
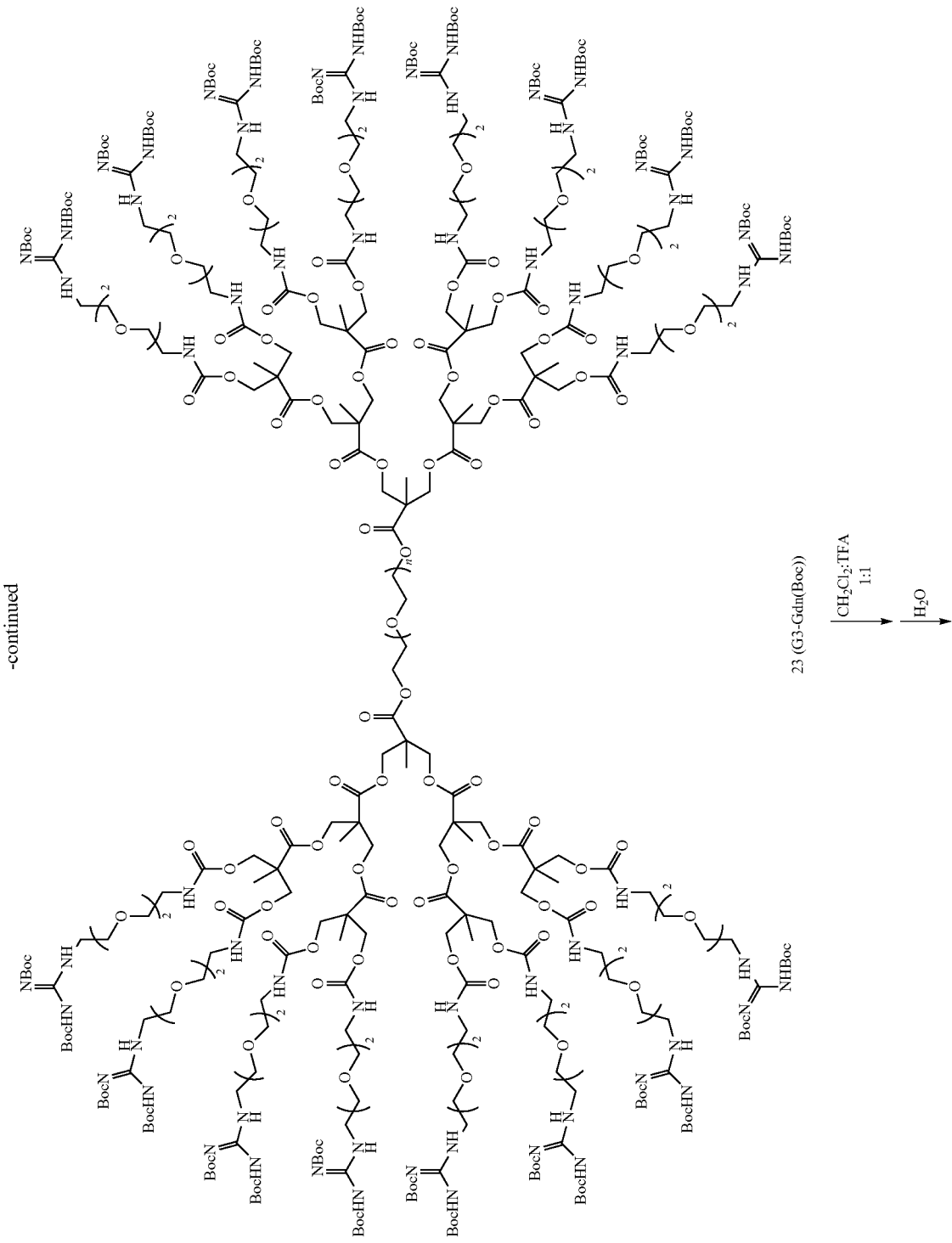

-continued
[Chemical Formula 10]
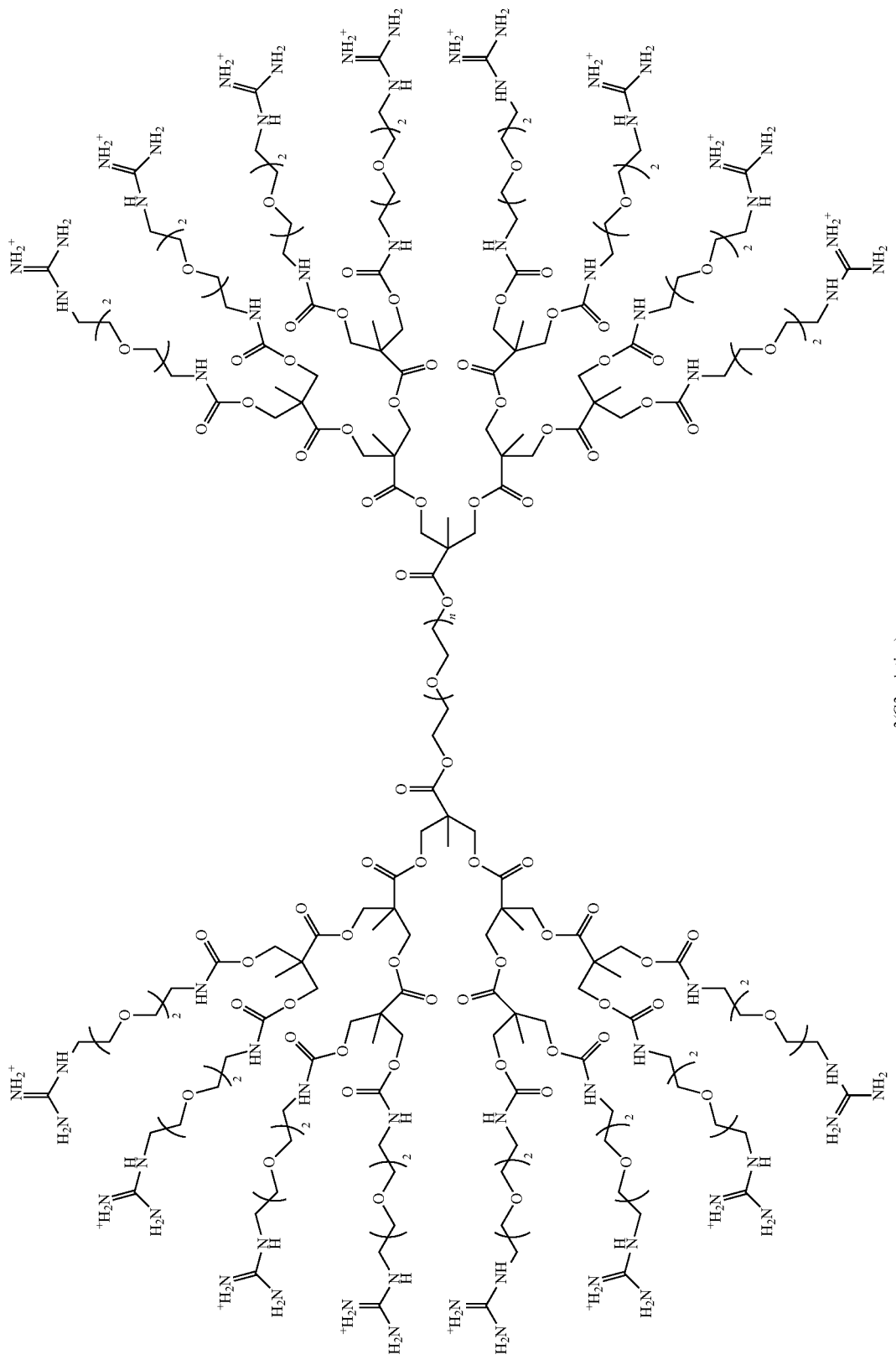
3(G3 solution)

(1) Production of Compound 21 (G3-NH(Boc))

1.0 g (0.08 mmol, 1 eq.) of Compound 11 (G3-OH) was dissolved in 5.0 mL of dichloromethane, added with 1.0 mL of pyridine and 1.6 g (8.0 mmol, 100 eq.) of 4-nitrophenylchloroformate, and then reacted by stirring at room temperature for 12 hours. The reaction solution was poured in diethyl ether to precipitate Compound 20, which was then purified. Compound 20 was dissolved in 6.0 mL of benzene, added with 0.29 g (2.12 mmol, 26 eq.) of 4-(dimethylamino)pyridine and 1.4 g of tert-butyl 2-(2-(2-aminoethoxy)ethoxy)ethylcarbamate, and then reacted by stirring at room temperature for 12 hours. The reaction solution was poured in diethyl ether to obtain 0.83 g of Compound 21 as a white solid (yield 58%).

$^1$H-NMR (270 MHz, CDCl$_3$) δ:
1.17 (s, 24), 1.23 (s, 18), 1.42 (s, 144),
3.64 (bs, ~1200), 4.16 (t, 32, J=5.0).
MALDI-TOF-MS: [M]$^+$=13535.

(2) Production of Compound 23 (G3-Gdn(Boc))

0.3 g of Compound 21 was dissolved in 4 mL of a mixed solvent of trifluoroacetic acid and dichloromethane (1:1), and stirred for 5 hours at room temperature to remove the protective group. Subsequently, the reaction solution was poured in diethyl ether to obtain Compound 22 as a precipitate. Thus-obtained Compound 22 was dissolved in 8.0 mL of dichloromethane, added with 1.5 mL of triethylamine and 0.20 g of N,N'-di(tert-butyloxycarbonyl)-N''-trifluoromethane sulfonylguanidine, and then reacted by stirring at room temperature for 8 hours. The reaction solution was poured in diethyl ether to obtain 0.21 g of Compound 29 as a white solid (yield 59%).

$^1$H-NMR (270 MHz, CDCl$_3$) δ:
1.16 (s, 24), 1.21 (s, 18), 1.47 (s, 288),
3.64 (bs, ~1200), 4.14 (t, 32, J=5.0).
MALDI-TOF-MS: [M]$^+$=14106.

(3) Production of Compound 3 (G3 (Solution))

0.036 g of Compound 23 was dissolved in 0.50 mL of a mixed solvent of trifluoroacetic acid and dichloromethane (1:1), and stirred at room temperature for 6 hours to remove the protective group, therefore obtaining Compound 3 (G3). The reaction was followed by NMR and complete loss of the signal at 1.47 verified the removal of the protective group. The reaction solution was subjected to high vacuum to remove the solvent and the by-products. After adding 1.0 mL of pure water, an aqueous solution of 3% by weight of G3 was used as it is for production of a hydrogel.

Example 5

Production of Hydrogel (2% G3-Clay) Based on Self-Agglomeration

An aqueous solution of 3% by weight of G3, which has been produced in Example 4, was diluted with pure water to give a 0.15% aqueous solution of G3. Then, the clay nano sheet (trade name: LAPONITE XLG, manufactured by Rockwood Additives Limited) (hectorite) was added to the aqueous solution to have an amount of 2% by weight and stirred. It was a transparent solution at the beginning of stirring, but within 5 minutes it turned into a hydrogel. The resulting hydrogel was named 2% G3-Clay. Water content of this gel was 97.9%.

Example 6

Production of Hydrogel (3% G3-Clay) Based on Self-Agglomeration

An aqueous solution of 3% by weight of G3, which has been produced in Example 4, was diluted with pure water to give a 0.23% aqueous solution of G3. Then, the clay nano sheet (trade name: LAPONITE XLG, manufactured by Rockwood Additives Limited) was added to the aqueous solution to have an amount of 3% by weight and stirred. It was a transparent solution at the beginning of stirring, but within 5 minutes it turned into a hydrogel. The resulting hydrogel was named 3% G3-Clay. Water content of this gel was 96.3%.

Example 7

Production of Hydrogel (4% G3-Clay) Based on Self-Agglomeration

2% G3-Clay hydrogel produced in Example 5 was dehydrated at 80° C. until the concentration of clay nano sheet reaches 4% to produce a hydrogel. The resulting hydrogel was named 4% G3-Clay. Water content of this gel was 95.7%.

Example 8

Production of Hydrogel (5% G3-Clay) Based on Self-Agglomeration

2% G3-Clay hydrogel produced in Example 5 was dehydrated at 80° C. until the concentration of clay nano sheet reaches 5% to produce a hydrogel. The resulting hydrogel was named 5% G3-Clay. Water content of this gel was 94.6%.

Example 9

Production of Hydrogel (Clay-G1) Based on Self-Agglomeration

An aqueous solution of 3% by weight of G1, which has been produced in Example 2, was diluted with pure water to give a 0.15% aqueous solution of G1. Then, the clay nano sheet (trade name: LAPONITE XLG, manufactured by Rockwood Additives Limited) was added to the aqueous solution to have an amount of 2% by weight and stirred. It was a transparent solution at the beginning of stirring, but within 5 minutes it turned into a hydrogel. Concentration of the guanidine group in the hydrogel was 0.5 mM. The resulting hydrogel was named Clay-G1. Water content of this gel was 97.9%.

Example 10

Production of Hydrogel (Clay-G2) Based on Self-Agglomeration

In order to determine the generation effect of the dendrons attached to both terminals of the polyethylene glycol, an aqueous solution of 3% by weight of G2, which has been produced in Example 3, was diluted with pure water to give a 0.078% aqueous solution of G2 in which the concentration of the guanidine group in the hydrogel is 0.5 mM. Then, the clay nano sheet (trade name: LAPONITE XLG, manufactured by Rockwood Additives Limited) was added to the aqueous solution to have an amount of 2% by weight and stirred. It was a transparent solution at the beginning of stirring, but within 5 minutes it turned into a hydrogel. The resulting hydrogel was named Clay-G2. Water content of this gel was 97.9%.

Example 11

Production of Hydrogel (Clay-G3) Based on Self-Agglomeration

In order to determine the generation effect of the dendrons attached to both terminals of the polyethylene glycol, an aqueous solution of 3% by weight of G3, which has been produced in Example 4, was diluted with pure water to give a 0.043% aqueous solution of G3 in which the concentration of the guanidine group in the hydrogel is 0.5 mM. Then, the clay nano sheet (trade name: LAPONITE XLG, manufactured by Rockwood Additives Limited) was added to the aqueous solution to have an amount of 2% by weight and stirred. It was a transparent solution at the beginning of stirring, but within 5 minutes it turned into a hydrogel. The resulting hydrogel was named Clay-G3. Water content of this gel was 98.0%.

Example 12

Production of Hydrogel (1% G3-Clay-ASAP) Based on Self-Agglomeration

An aqueous solution containing 0.03% by weight of sodium polyacrylate (ASAP) (sodium polyacrylate manufactured by Wako Pure Chemical Industries, Ltd., polymerization degree of 22,000 to 70,000, high viscosity (Catalogue No. 196-02955)) and 1% by weight of the clay nano sheet (trade name: LAPONITE XLG, manufactured by Rockwood Additives Limited) was stirred to give a transparent viscous liquid. Then, G3 was added to the viscous liquid to have an amount of 0.075% and stirred. As a result, within 5 minutes it turned into a hydrogel. The resulting hydrogel was named 1% G3-Clay-ASAP. Water content of this gel was 98.9%.

Example 13

Production of Hydrogel (2% G3-Clay-ASAP) Based on Self-Agglomeration

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, G3 was added to the viscous liquid to have an amount of 0.15% and stirred. As a result, within 5 minutes it turned into a hydrogel. The resulting hydrogel was named 2% G3-Clay-ASAP. Water content of this gel was 97.8%.

Example 14

Production of Hydrogel (3% G3-Clay-ASAP) Based on Self-Agglomeration

An aqueous solution containing 0.09% by weight of ASAP and 3% by weight of the clay nano sheet (trade name: LAPONITE XLG, manufactured by Rockwood Additives Limited) was stirred to give a transparent viscous liquid. Then, G3 was added to the viscous liquid to have an amount of 0.23% and stirred. As a result, within 5 minutes it turned into a hydrogel. The resulting hydrogel was named 3% G3-Clay-ASAP. Water content of this gel was 96.7%.

Example 15

Production of Hydrogel (4% G3-Clay-ASAP) Based on Self-Agglomeration

2% G3-Clay-ASAP hydrogel produced in Example 13 was dehydrated at 80° C. until the concentration of clay nano sheet reaches 4% to produce a hydrogel. The resulting hydrogel was named 4% G3-Clay-ASAP. Water content of this gel was 95.6%.

Example 16

Production of Hydrogel (5% G3-Clay-ASAP) Based on Self-Agglomeration

2% G3-Clay-ASAP hydrogel produced in Example 13 was dehydrated at 80° C. until the concentration of clay nano sheet reaches 5% to produce a hydrogel. The resulting hydrogel was named 5% G3-Clay-ASAP. Water content of this gel was 94.5%.

Example 17

Production of Hydrogel (Clay-G1-ASAP) Based on Self-Agglomeration

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, G1 was added to the viscous liquid to have an amount of 0.15% and stirred. As a result, within 5 minutes it turned into a hydrogel. Concentration of the guanidine group in the hydrogel was 0.5 mM. The resulting hydrogel was named Clay-G1-ASAP. Water content of this gel was 97.8%.

Example 18

Production of Hydrogel (Clay-G2-ASAP) Based on Self-Agglomeration

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, in order to determine the generation effect of the dendrons attached to both terminals of the polyethylene glycol, 0.078% of G2 was added to the viscous liquid so that the concentration of the guanidine group in the hydrogel becomes 0.5 mM. As a result of stirring, within 5 minutes it turned into a hydrogel. The resulting hydrogel was named Clay-G2-ASAP. Water content of this gel was 97.9%.

Example 19

Production of Hydrogel (Clay-G3-ASAP) Based on Self-Agglomeration

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, in order to determine the generation effect of the dendrons attached to both terminals of the polyethylene glycol, 0.043% of G3 was added to the viscous liquid so that the concentration of the guanidine group in the hydrogel becomes 0.5 mM. As a result of stirring, within 5 minutes it turned into a hydrogel. The resulting hydrogel was named Clay-G3-ASAP. Water content of this gel was 97.9%.

Example 20

5 Microliters of 2% G3-Clay-ASAP hydrogel of Example 13 was weighed, and with development on a porous carbon grid (Lacey-substrate-Ted Pella Ltd.) in a constant temperature and humidity chamber wherein the humidity is maintained at 97 to 99% to prevent evaporation of moisture, a thin film was produced. The remaining liquid was removed by treating with a filter paper for 2 to 3 seconds, and the thin film was immediately solidified by immersing in liquefied ethane that has been cooled by liquid nitrogen. After that, by using a Cryo Transfer Device, it is transferred to GATAN 626 cryo-holder and photographed with SC 1000 CCD camera (manufactured by GATAN, Inc.) attached to a transmission electron microscope (JEOL JEM-2010, 120 kV). As a result, TEM image shown in FIG. 2 was obtained. From FIG. 2, it is found that the clay nano sheets are linked to each other via the polymer dendronized both terminals thereof so that they are entangled with each other and present in a homogeneously dispersed state.

Example 21

Viscoelasticity Measurement

Effect of Dendrimer

Dynamic viscoelasticity of each of Clay-G1, Clay-G2, and Clay-G3 hydrogels, that are produced in Example 9, Example 10, and Example 11, was measured by using ARES-RFS rheometer (manufactured by TA INSTRUMENTS) equipped with a 25 mm parallel disc under the constant strain condition ($\gamma=1\%$). As a result, the frequency distribution shown in FIG. 3 was obtained. It was found that the storage modulus (G') and loss modulus (G") of the hydrogels have a plateau region which does not depend on the frequency. And in the plateau region, G' is bigger than G" (G'>G") and a gel characteristic of a quasi solid state is exhibited. The G' which indicates the strength of the hydrogel increases in accordance with the increase in the generation number of the dendron even when the polyethylene glycol having the dendrons at both terminals thereof, that is used for the production of the hydrogel, has the same guanidine cation concentration, and therefore the effect of the dendron is shown.

Example 22

Viscoelasticity Measurement

Effect of Dendrimer

The measurement was carried out in the same manner as in Example 21 except that Clay-G1-ASAP, Clay-G2-ASAP, and Clay-G3-ASAP hydrogels containing an anionic polymer, that are produced in Example 17, Example 18, and Example 19, are used. The results shown in FIG. 4 were obtained. It was found that the effect of the dendrimer is shown also for the strength of these hydrogels, and at the same time, an increase in the strength (G') of the hydrogel is obtained according to the addition of anionic polymers.

Example 23

Viscoelasticity Measurement

Effect of Clay Nano Sheet

The measurement was carried out in the same manner as in Example 21 except that 2% G3-Clay, 3% G3-Clay, 4% G3-Clay, and 5% G3-Clay hydrogels that are produced in Examples 5 to 8, are used. The results shown in FIG. 5 were obtained. It was found that the strength (G') of the hydrogels increases in accordance with the concentration increase of the clay nano sheet, and it is as high as 0.1 MPa for 5% G3-Clay.

Example 24

Viscoelasticity Measurement

Effect of Clay Nano Sheet

The measurement was carried out in the same manner as in Example 21 except that 1% G3-Clay-ASAP, 2% G3-Clay-ASAP, 3% G3-Clay-ASAP, 4% G3-Clay-ASAP, and 5% G3-Clay-ASAP hydrogels that are produced in Examples 12 to 16, are used. The results shown in FIG. 6 were obtained. It was found that the strength (G') of the hydrogels increases in accordance with the concentration increase of the clay nano sheet, and it is as high as 0.5 MPa for 5% G3-Clay-ASAP.

Example 25

Viscoelasticity Measurement

Strain Dependency

The viscoelasticity measurement was carried out by using the same device as in Example 21 for 5% G3-Clay-ASAP hydrogel produced in Example 16 to evaluate the strain dependency. The results shown in FIG. 7 were obtained. As a result, it was found that 5% G3-Clay-ASAP is a quasi solid gel which has the storage modulus (G') of 0.5 MPa under low strain condition. However, G' starts to rapidly decrease with the strain exceeding the critical strain ($\gamma=9\%$), and as a result the gel is disrupted to yield a quasi liquid state.

Example 26

Viscoelasticity Measurement

Characteristic of High Speed Viscoelasticity Return—Self-Restoring Property

Dynamic viscoelasticity of 5% G3-Clay-ASAP hydrogel that is produced in Example 16 was measured by using the same device as in Example 21. The results shown in FIG. 8 were obtained. Under the condition including frequency ($\omega$) of 6 rad/s (1 Hz) and strain ($\gamma$) of 0.1%, the storage modulus (G') was about 0.5 MPa and the loss tangent (tan $\delta$=G"/G') value was about 0.4 to 0.5, indicating a quasi solid property (see, FIG. 8). When 100% strain was applied to the gel while maintaining the same frequency of 6 rad/s, the storage modulus (G') was deceased to about 5 KPa, showing a quasi liquid property with the loss tangent (tan $\delta$=G"/G') value of 3 to 4. Further, when 100% strain load is continuously applied for 300 seconds and then immediately the dynamic viscoelasticity is measured after adjusting the strain back to 0.1%, the storage modulus (G') was immediately restored to 0.5 MPa. Further, this high speed return behavior has a repeating characteristic showing that it was not impaired even after continuously repeating three times the cycle of low strain load (0.1%) and high strain load (100%). From such result, it was found that the hydrogel of the invention has a specific high speed return behavior. Although a hydrogel with the same behavior has been reported before, under low strain condition the hydrogel of the invention has storage modulus (0.5 MPa) that is one digit higher than that of the oligomeric electrolyte hydrogel (Non-patent Document 9 (Yoshida, M., Koumura, N., Misawa, Y., Tamaoki, N., Matsumoto, H., Kawanami, H., Kazaoui, S., Minami, N. Oligomeric electrolyte as a multifunctional gelator J. Am. Chem. Soc. 129, 11039-11041 (2007))), 2 to 3 digits higher than that of copolypeptide hydrogel (Non-patent Document 10 (Nowak, A. P., Breedveld, V., Pakstis, L., Bulent, O., Pine, D. J., Pochan, D., Deming, T. J. Rapid recovering hydrogel scaffolds from self-assembling diblock copolypeptide amphiphiles Nature 417, 424-428 (2002))), and almost 2 digits higher than that of the hydrogel consisting of an ionic organic compound which contains a quaternary ammonium cation formed of a heterocyclic compound such as pyridine (Patent Document 1 (WO2006/082768)).

From the results above, it was shown that the hydrogel of the invention has a high self-restoring property.

Example 27

Production of Myoglobin-Containing Hydrogel

An aqueous solution of 3% by weight of G3, which has been produced in Example 4, was diluted with pure water to give a 0.043% aqueous solution of G3 which contains the guanidine group at a concentration of 0.5 mM in the hydrogel. Then, the clay nano sheet (trade name: LAPONITE XLG, manufactured by Rockwood Additives Limited) was added to the aqueous solution to have an amount of 2% by weight. Subsequently, myoglobin (Mb) was added thereto to have 5 µM of Mb concentration and stirred to give a hydrogel, which was named G3-Clay-Mb. As a result of analyzing the gel using an ultraviolet and visible spectrophotometer, an absorption based on soret band of myoglobin was found at 405 nm, which corresponds to the same wavelength of a soret band from free myoglobin. Thus, it was found that myoglobin undergoes no structural change even when it is introduced to a hydrogel.

Example 28

Production of Myoglobin-Containing Hydrogel

An aqueous solution of 3% by weight of G1, which has been produced in Example 2, was diluted with pure water to give a 0.15% aqueous solution of G1 which contains the guanidine group at a concentration of 0.5 mM in the hydrogel. Then, the clay nano sheet (trade name: LAPONITE XLG, manufactured by Rockwood Additives Limited) was added to the aqueous solution to have an amount of 2% by weight. Subsequently, myoglobin (Mb) was added thereto to have 5 µM of Mb concentration and stirred to give a hydrogel, which was named G1-Clay-Mb. As a result of analyzing the gel using an ultraviolet and visible spectrophotometer, an absorption based on soret band of myoglobin was found at 405 nm, which corresponds to the same wavelength of a soret band from free myoglobin. Thus, it was found that myoglobin undergoes no structural change even when it is introduced to a hydrogel.

Example 29

Production of Myoglobin-Containing Hydrogel

An aqueous solution of 3% by weight of G2, which has been produced in Example 3, was diluted with pure water to give a 0.078% aqueous solution of G2 which contains the guanidine group at a concentration of 0.5 mM in the hydrogel. Then, the clay nano sheet (trade name: LAPONITE XLG, manufactured by Rockwood Additives Limited) was added to the aqueous solution to have an amount of 2% by weight. Subsequently, myoglobin (Mb) was added thereto to have 5 µM of Mb concentration and stirred to give a hydrogel, which was named G2-Clay-Mb. As a result of analyzing the gel using an ultraviolet and visible spectrophotometer, an absorption based on soret band of myoglobin was found at 405 nm, which corresponds to the same wavelength of a soret band from free myoglobin. Thus, it was found that myoglobin undergoes no structural change even when it is introduced to a hydrogel.

Example 30

Production of Albumin-Containing Hydrogel

An aqueous solution of 3% by weight of G3, which has been produced in Example 4, was diluted with pure water to give a 0.043% aqueous solution of G3 which contains the guanidine group at a concentration of 0.5 mM in the hydrogel. Then, the clay nano sheet (trade name: LAPONITE XLG, manufactured by Rockwood Additives Limited) was added to the aqueous solution to have an amount of 2% by weight. Subsequently, albumin (BSA) was added thereto to have 3 µM of BSA concentration and stirred to give a hydrogel, which was named G3-Clay-BSA. As a result of analyzing the gel using an ultraviolet and visible spectrophotometer, an absorption based on soret band of albumin was found at 280 nm, which corresponds to the same wavelength of a soret band from free albumin. Thus, it was found that albumin undergoes no structural change even when it is introduced to a hydrogel.

Example 31

Production of myoglobin-containing hydrogel

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, 0.043% of G3 was added to the viscous liquid so that the concentration of the guanidine group in the hydrogel becomes 0.5 mM. Subsequently, myoglobin (Mb) was added thereto to have 5 µM of Mb concentration and stirred to give a hydrogel, which was named G3-Clay-ASAP-Mb. As a result of analyzing the gel using an ultraviolet and visible spectrophotometer, an absorption based on soret band of myoglobin was found at 405 nm, which corresponds to the same wavelength of a soret band from free myoglobin. Thus, it was found that myoglobin undergoes no structural change even when it is introduced to a hydrogel.

Example 32

Production of albumin-containing hydrogel

An aqueous solution containing 0.06% by weight of ASAP and 2% by weight of the clay nano sheet (trade name: LAPONITE XLG, manufactured by Rockwood Additives Limited) was stirred to give a transparent viscous liquid. Then, 0.043% of G3 was added to the viscous liquid so that the concentration of the guanidine group in the hydrogel becomes 0.5 mM. Subsequently, albumin (BSA) was added thereto to have 3 µM of BSA concentration and stirred to give a hydrogel, which was named G3-Clay-ASAP-BSA. As a result of analyzing the gel using an ultraviolet and visible spectrophotometer, an absorption based on soret band of albumin was found at 280 nm, which corresponds to the same wavelength of a soret band from free albumin. Thus, it was found that albumin undergoes no structural change even when it is introduced to a hydrogel.

Example 33

Release of Myoglobin from Myoglobin-Containing Hydrogel

The G3-Clay-Mb hydrogel produced in Example 27 was centrifuged at 15000 rpm and the isolated myoglobin concentration in water was analyzed based on the absorption of the soret band at 405 nm, and then the released myoglobin ratio was calculated ($1^{st}$ release). Subsequently, the dehydrated hydrogel was treated with water, centrifuged again at 15000 rpm, and then the second released myoglobin ratio ($2^{nd}$ release) was calculated from the concentration of isolated myoglobin in water. For G1-Clay-Mb and G2-Clay-Mb hydrogels that are produced from Examples 28 and Example 29, the same measurement was carried out to obtain the results shown in FIG. 9. From FIG. 9, it was found that the amount of released myoglobin is very small and the released ratio is decreased as the generation of dendron group in the polymer which has dendron groups at both terminals thereof increases.

Example 34

Release of Protein from Various Protein-Containing Hydrogels

Each of G3-Clay-Mb, G3-Clay-BSA, G3-Clay-ASAP-Mb, and G3-Clay-ASAP-BSA hydrogels that are produced in Example 27, Example 30, Example 31, and Example 32 was centrifuged at 15000 rpm and the concentration of the isolated myoglobin or albumin concentration in water was analyzed based on the absorption at 405 nm of the soret band or 280 nm, and then the released myoglobin or albumin ratio was calculated and the results shown in FIG. 8 were obtained. As a result, it was found that both of the released myoglobin ratio and the released albumin ratio were 5% or less.

Example 35

Activity of Myoglobin Introduced to Hydrogel

It is known that myoglobin catalyzes an oxidation of orthophenylene diamine (o-phenylene diamine (OPD)) by hydrogen peroxide ($H_2O_2$). Thus, having this reaction as a model reaction, it was determined whether or not the myoglobin introduced to the hydrogel maintains its activity for oxidation of orthophenylene diamine. Specifically, to an aqueous solution containing 25.0 mM of $H_2O_2$ and 10.0 mM of OPD, myoglobin was added to the concentration of 0.5 µM and the absorption increase at 420 nm ($\epsilon_{420nm}=16300$ $M^{-1} \cdot cm^{-1}$), which corresponds to the reaction product, i.e., 2,3-diamino-5,10-dihydrophenazine, was determined every 10 seconds for 3 minutes. From the slope obtained, the reaction rate was calculated and taken as an activity of free myoglobin. Further, to an aqueous solution containing 25.0 mM of $H_2O_2$ and 10.0 mM of OPD, G3-Clay-Mb or G3-Clay-ASAP-Mb hydrogel of Example 27 or Example 31 was added to have the myoglobin concentration of 0.5 µM, and then the activity of myoglobin introduced to the hydrogel was obtained according to the same method as above for free myoglobin. Then, the ratio compared to the activity of free myoglobin obtained above was calculated, and the results shown in FIG. 11 were obtained. It was found that the activity of the myoglobin in G3-Clay-Mb is about 80% of the activity of free myoglobin while the activity of the myoglobin in G3-Clay-ASAP-Mb is about 71% of the activity of free myoglobin. Although there is a slight decrease compared to the activity of free myoglobin, it is believed that the decrease is caused by the difficulty of diffusion of a reaction substrate and reaction product in the hydrogel. To verify this, the same measurement was carried out for Clay-Mb, ASAP-Mb, and G3-Mb, and the activity of myoglobin in each environment was obtained and shown in FIG. 11. As clearly shown in FIG. 11, it was found that the activity of the myoglobin in the systems of Clay-Mb and ASAP-Mb is 98% or 96% of the activity of free myoglobin, respectively, and the clay nano sheet and ASAP has no effect on the activity of myoglobin. Meanwhile, the activity of the myoglobin in the G3-Mb system was only 35% of the activity of free myoglobin. It is believed that such dramatic decrease in myoglobin activity in this system is due to the presence of the guanidine group in a great excess amount (500 µM) in G3 compared to the myoglobin (5 µM), showing an influence of the guanidine group on the myoglobin activity. However, as the most of the guanidine group are present on the surface of the clay nano sheet in the systems of G3-Clay-Mb and G3-Clay-ASAP-Mb, these systems are not affected by the above-mentioned effect. Further, although the myoglobin activity in the system of G3-Clay-Mb is slightly higher than that of G3-Clay-ASAP-Mb, it is believed that the structure of hydrogel is slightly weaker in G3-Clay-Mb compared to in G3-Clay-ASAP-Mb, and therefore it is less likely affected by diffusion, and it is not contradictory to the phenomenon that the strength of G3-Clay-ASAP gel is higher than that of G3-Clay.

Example 36

Shape-Retaining Property of Hydrogel

According to the same method as in Example 16, 5% G3-Clay-ASAP hydrogel having a heart shape was produced within a frame, as shown in FIG. 12a. The resulting hydrogel was immersed in tetrahydrofuran (THF). In general, a physically crosslinked hydrogel loses its shape when it is immersed in THF. However, the hydrogel of the invention maintained the heart shape as shown in FIG. 12b. Further, although the gel was shrunken all around when it is dried, the overall heart shape was maintained as shown in FIG. 12c. Further, when the dried gel is added into water, it is restored to the heart-shape hydrogel shown in FIG. 12a.

INDUSTRIAL APPLICABILITY

The hydrogel of the invention that is produced with a novel material for hydrogel containing the polyionic dendrimer of the invention and the clay minerals (i.e., clay) can contain water at high water content (i.e., at least 940), is a transparent gel with high strength, and has a self-restoring property, a shape-retaining property, and a characteristic of maintaining behavior of a protein such as a protein having a physiologically activity or an enzymatically activity without modifying the behavior of the protein. Thus, the hydrogel of the invention is very useful not only for the conventional use of hydrogel but also for various industrial fields including pharmaceuticals, food products, cosmetics, hygienic products, and the like, and therefore it has an industrial applicability.

The invention claimed is:

1. A hydrogel comprising:
   (a) a clay mineral, and
   (b) a polyionic dendrimer, wherein the polyionic dendrimer comprises:
      (i) a polyalkylene glycol as a core of the polyionic dendrimer;
      (ii) polyester dendrons attached to both terminals of the polyalkylene glycol; and
      (iii) a cationic group which is bonded to a surface of the dendrons and is selected from the group consisting of a guanidine group, a thiourea group, and an isothiourea group; and
   wherein a water content in the hydrogel is 80% or more.

2. The hydrogel according to claim 1, wherein the polyester is a polyester composed of a saturated aliphatic carboxylic acid having 3 to 10 carbon atoms in which two or more hydroxyl groups are symmetrically substituted to have symmetric branching.

3. The hydrogel according to claim 1, wherein the polyalkylene glycol is a polyethylene glycol.

4. The hydrogel according to claim 1, wherein the cationic group which is selected from the group consisting of a guanidine group, a thiourea group, and an isothiourea group is bonded to the surface of the dendrons via a polyether group.

5. The hydrogel according to claim 1, wherein the polyionic dendrimer is represented by formula 1:

number of a linker group for introducing cationic groups to the surface and is from 1 to 6; g is the generation of the dendrons and is from 1 to 5; R is a cationic group selected from the group consisting of a guanidine group, a thiourea group, and an isothiourea group; and X is a hydrogen atom or a $C_1$-$C_7$ alkyl group.

6. The hydrogel according to claim 5, wherein X is a methyl group.

7. The hydrogel according to claim 1, wherein the cationic group selected from the group consisting of a guanidine group, a thiourea group, and an isothiourea group is a cationic group represented by formula 2, formula 3, or formula 4:

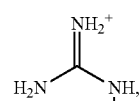

Formula 2

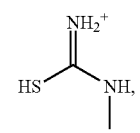

Formula 3

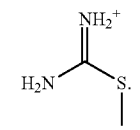

Formula 4

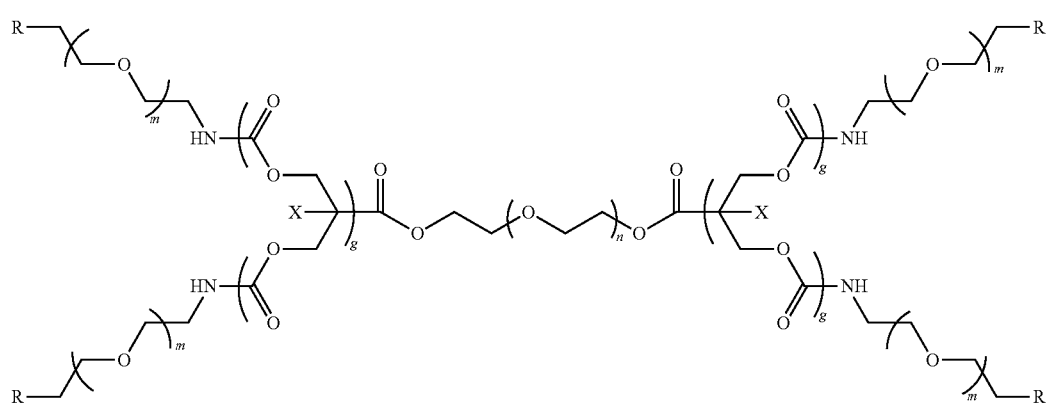

Formula 1 wherein n is the repeating number of polyethylene glycol in the core and is from 20 to 100,000; m is the repeating 8. The hydrogel according to claim 1, wherein the polyionic dendrimer is represented by formula 5:

Formula 5
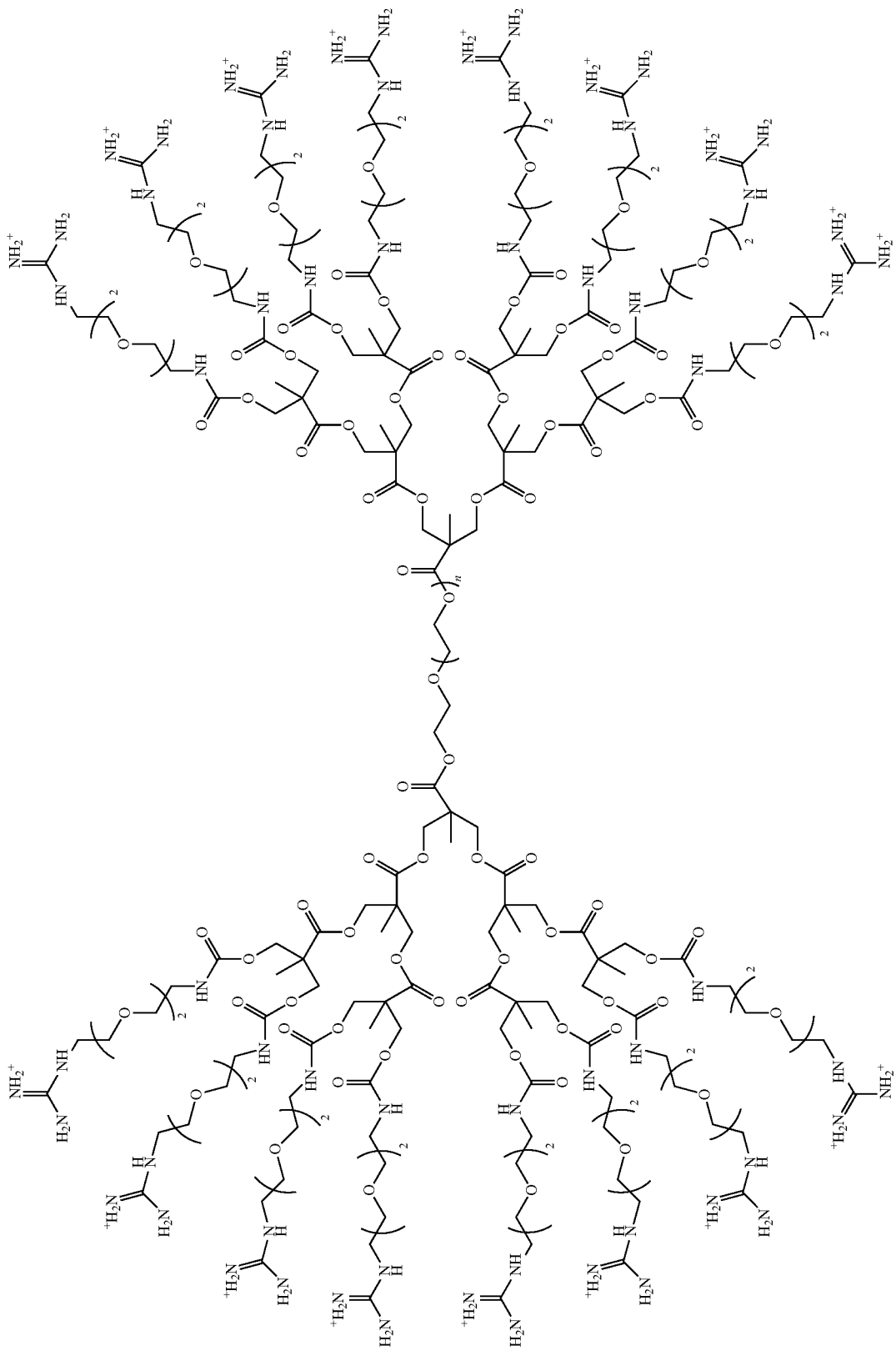

wherein n is from 20 to 100,000.

9. The hydrogel according to claim 1, further comprising an alkali metal salt of polyacrylic acid or polymethacrylic acid as a linear polymer having an ionic side chain.

10. The hydrogel according to claim 9, wherein the alkali metal salt is a sodium salt.

11. The hydrogel according claim 1, wherein the clay mineral is a water-swellable smectite.

12. The hydrogel according to claim 1, wherein the clay mineral is one or more kinds selected from the group consisting of montmorilonite, hectorite, saponite, bidelite, mica, and synthetic mica.

13. The hydrogel according to claim 1, wherein the clay mineral is a hectorite.

14. A protein-containing hydrogel, comprising:
the hydrogel according to claim 1; and
a physiologically active protein in the hydrogel.

15. The protein-containing hydrogel according to claim 14, wherein the physiologically active protein is myoglobin or albumin.

16. A material for a hydrogel, comprising:
(a) a clay mineral;
(b) an alkali metal salt of polyacrylic acid or polymethacrylic acid as a linear polymer having an ionic side chain; and
(c) a polyionic dendrimer, wherein the polyionic dendrimer comprises:
  (i) a polyalkylene glycol as a core of the polyionic dendrimer;
  (ii) polyester dendrons attached to both terminals of the polyalkylene glycol; and
  (iii) a cationic group which is bonded to a surface of the dendrons and is selected from the group consisting of a guanidine group, a thiourea group, and an isothiourea group; and
wherein the polyionic dendrimer and the clay mineral can be mixed with water to produce the hydrogel.

* * * * *